(12) United States Patent
Smeitink et al.

(10) Patent No.: US 11,357,767 B2
(45) Date of Patent: Jun. 14, 2022

(54) COMPOUNDS FOR USE IN TREATING DEPRESSION AND MIGRAINE

(71) Applicant: Khondrion IP B.V., Beuningen (NL)

(72) Inventors: Johannes Albertus Maria Smeitink, Beuningen (NL); Julien David Beyrath, Nijmegen (NL)

(73) Assignee: Khondrion IP B.V., Beuningen (NL)

( * ) Notice: Subject to any disclaimer, the term of this patent is extended or adjusted under 35 U.S.C. 154(b) by 88 days.

(21) Appl. No.: 16/765,480

(22) PCT Filed: Nov. 22, 2018

(86) PCT No.: PCT/EP2018/082143
§ 371 (c)(1),
(2) Date: May 20, 2020

(87) PCT Pub. No.: WO2019/101825
PCT Pub. Date: May 31, 2019

(65) Prior Publication Data
US 2020/0289491 A1 Sep. 17, 2020

(30) Foreign Application Priority Data
Nov. 22, 2017 (EP) .................................... 17203136

(51) Int. Cl.
| | | |
|---|---|---|
| A61K 31/453 | (2006.01) | |
| A61P 25/24 | (2006.01) | |
| A61P 25/06 | (2006.01) | |
| A61K 9/00 | (2006.01) | |
| A61K 31/452 | (2006.01) | |
| A61K 45/06 | (2006.01) | |

(52) U.S. Cl.
CPC .......... *A61K 31/453* (2013.01); *A61K 9/0053* (2013.01); *A61K 31/452* (2013.01); *A61K 45/06* (2013.01); *A61P 25/06* (2018.01); *A61P 25/24* (2018.01)

(58) Field of Classification Search
CPC ...... A61K 31/425; A61K 31/435; A61P 25/24
See application file for complete search history.

(56) References Cited

FOREIGN PATENT DOCUMENTS

| WO | WO2014/011047 A1 | 1/2014 |
|---|---|---|
| WO | WO2017/060432 A1 | 4/2017 |

OTHER PUBLICATIONS

Maiese K.:"Mitochondria "Mood Altering Organelles" That Impact Disease Throughout the Nervous System". Current Neurovascular Research, vol. 12, No. 4, 2015, pp. 309-311, 2015, pp. 309-311.
Hollander E.: Brain and Body: Mitochondrial Disease. Fever. and Impulsivity. CNS Spectr . . . vol. 12. No. 6. 2007. pp. 416-417.
Sparaco et al.:"Mitochondrial Dysfunction and Migraine: Evidence and Hypotheses". Cephalalgia. vol. 26. 2005. pp. 361-372.
Santander et al "Clinical and Genetic Manifestations of Chilean Patients With DNA Mitochondrial Disease". Journal of the Neurological Sciences, vol. 357. 1522. 2015. p. E442.
Ahmed, F. (2012). Headache disorders: differentiating and managing the common subtypes. Br. J. Pain 6: 124-32.
Ashina, S., et al., (2012). Depression and risk of transformation of episodic to chronic migraine. J. Headache Pain 13: 615-624.
Bansal, Y., and Kuhad, A. (2016). Mitochondrial Dysfunction in Depression. Curr. Neuropharmacol. 14: 610-618.
Fuller-Thomson, E., et al., (2013). Depress. Res. Treat. 2013: 1-10.
Goadsby, P.J., Lipton, R.B., and Ferrari, M.D. (2002). Migraine—Current Understanding and Treatment. N. Engl. J. Med. 346: 257-270.
Janssen, M.C.H. et al., 2018, Clin. Pharm. Ther. DOI: 10.1002/cpt.1197.
Kalra, A.A., and Elliott, D. (2007). Acute migraine: Current treatment and emerging therapies. Ther. Clin. Risk Manag. 3: 449-59.
Koene, S., et al., (2009). Major depression in adolescent children consecutively diagnosed with mitochondrial disorder. J. Affect. Disord. 114: 327-332.
Kraya, T., et al., (2017). Prevalence of Headache in Patients With Mitochondrial Disease: A Cross-Sectional Study. Headache J. Head Face Pain.
Obermann, M., and Holle, D. (2016). Recent advances in the management of migraine. F1000Research 5: 2726.
Verhaak, C., Laat, P. De, Koene, S., Tibosch, M., Rodenburg, R., Groot, I. De, et al. Quality of life, fatigue and mental health in patients with the m.3243A > G mutation and its correlates with genetic characteristics and disease manifestation.
Vollono, C., Primiano, G., Marca, G. Della, Losurdo, A., and Servidei, S. (2017). Migraine in mitochondrial disorders: Prevalence and characteristics. Cephalalgia 33310241772356.
Yang, Y., et al., (2016). Familial Aggregation of Migraine and Depression: Insights From a Large Australian Twin Sample. Twin Res. Hum. Genet. 19: 312-21.

*Primary Examiner* — Kevin E Weddington
(74) *Attorney, Agent, or Firm* — N.V. Nederlandsch Octrooibureau

(57) ABSTRACT

The invention relates to amide-derivatives of 6-hydroxy-2, 5,7,8-tetramethylchroman-2-carboxylic acid for use in a treatment for preventing or suppressing symptoms associated with mood disorders, headaches and migraine. The compounds of the invention can be used to treat any subject suffering from a mood disorder, headaches and/or migraine but can specifically be used to treat a mood disorder, headaches and/or migraine in patients suffering from a mitochondrial disease.

16 Claims, No Drawings

COMPOUNDS FOR USE IN TREATING DEPRESSION AND MIGRAINE

FIELD OF THE INVENTION

The present invention relates to the fields of human and veterinary medicine. The invention in particular relates to amide-derivatives of 6-hydroxy-2,5,7,8-tetramethylchroman-2-carboxylic acid for treating a mood disorder, headaches and/or migraine. The compounds of the invention can be used to treat any subject suffering from a mood disorder, headaches and/or migraine but can specifically be used to treat a mood disorder, headaches and/or migraine in patients suffering from a mitochondrial disease.

BACKGROUND ART

Migraine, a recurrent type of disabling headache accompanied by chronic and episodic manifestations, is one of the most complex neurological disorders (Goadsby et al. 2002). Migraine remains one of the most disabling disorders worldwide. A migraine is a seriously debilitating and usually unilateral form of episodic headache that can cause severe throbbing pain or a pulsing sensation, usually on just one side of the head. It is often accompanied by nausea, vomiting, and extreme sensitivity to light (photophobia), sound (phonophobia), and smells (osmophobia), sleep disruption, and depression. Migraine attacks can cause significant pain for hours to three days when untreated and can be so severe that the pain is disabling. Therapeutic management of migraine relies mainly on non-specific medical treatment and is affected by low patient adherence to the treatment regimens applied. Migraine is associated with a substantially reduced quality of life for the individual and a high level of economic burden for society. Migraines include cluster headaches and vascular headaches and are sometimes termed sick headaches or histamine headaches. Other, less common, types of migraine exist and include migraine with prolonged aura; migraine aura without headache; migraine with acute onset aura; basilar migraine which can be associated with vertigo, gait perturbations and/or loss of consciousness; ophthalmoplegic migraine associated with ocular paralysis, diplopia and/or ptosis; retinal migraine; and familial hemiplegic migraine associated with hemiparesis or hemiplegia. Pharmacological interventions for the management of migraine can be categorized into two general strategies. Acute treatment is a therapy used to stop an attack when it begins. Preventive treatment is a therapy used to reduce the number of attacks, lessen the intensity of pain, and prevent the onset of future attacks. Current treatment options often lack efficacy and induce various side effects, therefore there is still a high need for the development of new pharmacological approaches with higher therapeutic power for the treatment of migraines (Kalra and Elliott, 2007; Ahmed, 2012; Obermann and Holle, 2016).

Mood disorders are some of the most common mental illnesses. Some examples of mood disorders include Major Depressive Disorder, Bipolar disorder, Seasonal affective disorder, Cyclothymic disorder, Premenstrual dysphoric disorder, Persistent depressive disorder (dysthymia), Disruptive mood dysregulation disorder, Depression related to medical illness, Depression induced by substance use or medication. Depression and anxiety are common mood disorders and can often co-occur. Depression is a psychological disorder characterized by dramatic decline in both mental and physical conditions. These disorders can be treated through psychotherapy and medications, such as anti-depressants. Unfortunately, current medications may take weeks to months to achieve their full effects and in the meantime, patients continue to suffer from their symptoms and continue to be at risk. Moreover, side effects from these medications can range from unpleasant to life-threatening; for instance, there can be an increased risk of suicide, hostility, and even homicidal behavior. Pharmacological treatments that have a rapid onset of antidepressant or anti-anxiety effects within hours or a few days and that are sustained are therefore desired.

Multiple cross-sectional studies have consistently observed that migraine often co-occurs with depression ((Ashina et al., 2012; Fuller-Thomson et al., 2013; Yang et al., 2016). For example, a large proportion of patients suffering from mitochondrial disease are suffering from migraine and mood disorders such as depression (Kraya et al. 2017; Verhaak et al. 2016; Koene et al. 2009; Bansal & Kuhad 2016; Vollono et al. 2017).

WO2014/011047 and WO2017/060432 disclose amide-derivatives of 6-hydroxy-2,5,7,8-tetramethylchroman-2-carboxylic acid, including KH176, for treating or preventing mitochondrial disorders and/or conditions associated with mitochondrial dysfunction. In the recent clinical trial KHENERGY (clinicaltrials.gov identifier NCT02909400), the study drug KH176 of the present invention was shown to significantly reduce depression symptoms in mitochondrial disease patients carry a mutation in the mitochondrial DNA. Additionally, patients participating in the KHENERGY study who previously chronically suffered from migraine all reported a reduction of the intensity and number of migraine events during the KH176 treatment period.

On the basis thereof, it is an object of the present invention to provide for novel methods of treatment of subjects suffering from mood disorders, headaches and/or migraine.

SUMMARY OF THE INVENTION

The present invention pertains to a compound represented by general structure (I):

(I)

wherein,
T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;
L is a linker between the amide nitrogen atom and the distal nitrogen atom comprising 1 to 10 optionally substituted backbone atoms selected from carbon, nitrogen and oxygen;
N* is represented by structure (IIa) or (IIb)

(IIa)

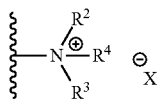

(IIb)

R¹ and R² are each independently selected from hydrogen (H), $C_1$-$C_6$ alkyl or $C_1$-$C_6$ alkenyl, or R¹ and R² are joined together and thus form a second linker between the amide nitrogen atom and the distal nitrogen atom, or R¹ is joined with a backbone atom of the linker L in a cyclic structure and/or R² is joined with a backbone atom of the linker L in a cyclic structure;

R³ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or R³ is absent when the distal nitrogen atom is part of an imine moiety; or optionally R³ is joined with a backbone atom of the linker L in a cyclic structure; and R⁴ is selected from hydrogen (H) or $C_1$-$C_6$ alkyl, wherein the alkyl moiety may be substituted with one or more halogen atoms or (halo)alkoxy moieties;

X is an anion, preferably a pharmaceutically acceptable anion, for use in treating, preventing or suppressing symptoms associated with at least one of: a) a mood disorder; and, b) headache and/or migraine.

Preferably, the compound is represented by structure (VI):

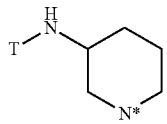

(VI)

wherein, N* is —NR³ or —N⁺R³R⁴X⁻, wherein T, X, R³, and R⁴ are as defined above.

In a compound of the invention, preferably T is represented by structure (IIIa) or (IIIb):

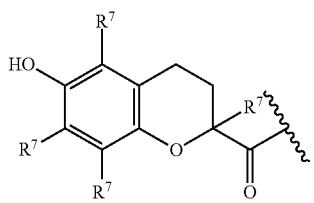

(IIIa)

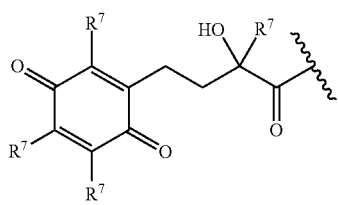

(IIIb)

wherein R⁷ is individually a $C_1$-$C_6$ alkyl moiety, preferably each R⁷ is methyl.

In a first aspect, the compounds of the invention are for use in treating, preventing or suppressing symptoms associated with a mood disorder, wherein preferably, the mood disorder comprises depression. Preferably, in the treatment, the use of the compound according to this aspect of the invention eliminates, reduces the severity of, and/or reduces the frequency of occurrence of at least one symptom of the mood disorder, preferably as determined using the Beck Depression Index. Preferably, the symptom of the mood disorder includes at least one of apathy, persistent feelings of sadness, feelings of hopelessness or helplessness, having low self-esteem, feeling inadequate, excessive guilt, feelings of wanting to die, loss of interest in usual activities or activities once enjoyed, difficulty with relationships, sleep disturbances, changes in appetite or weight, decreased energy, difficulty concentrating, a decrease in the ability to make decisions, suicidal thoughts or attempts, frequent physical complaints, running away or threats of running away from home, hypersensitivity to failure or rejection, irritability, hostility, or aggression. In one embodiment according to this aspect of the invention, the treatment further comprises the administration of an additional active agent selected from the group consisting of a norepinephrine reuptake inhibitor, a selective serotonin reuptake inhibitor, a tricyclic antidepressant, a monoamine oxidase inhibitor, and combinations thereof.

In a second aspect, the compounds of the invention are for use in treating, preventing or suppressing symptoms associated with headache and/or migraine, whereby, preferably, the headache comprises tension-type headaches and whereby the migraine comprises common migraine, classic migraine, familial hemiplegic migraine, sporadic hemiplegic migraine, migraine with brainstem aura, retinal migraine, recurrent migraine and chronic migraine. Preferably, in the treatment, the use of the compound according to this aspect of the invention eliminates, reduces the severity of, and/or reduces the frequency of occurrence of at least one symptom of tension-type headaches and/or migraine, which symptom preferably includes at least one of (moderate to severe) headaches, and associated symptoms including aura, blurred vision, nausea, vomiting, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, cold and moist feeling in appendages, and sensitivity to light, sound, or smell. In one embodiment according to this aspect of the invention, the treatment further comprises the administration of an additional active agent selected from the group consisting of a preventive migraine medication, an analgesic, a triptan and an ergotamine.

A compound for use according to both aspects of the invention preferably is administered in a total daily dose that is in the range of about 5 to 2000 mg, preferably about 20 to 800 mg, more preferably the total daily dose is in the range of between about 30 to 400 mg and most preferably the total daily dose is in the range of about 150 to 250 mg.

A compound for use according to both aspects of the invention preferably is administered orally. More preferably, the compound is administered in a solid form or in a liquid form, wherein preferably the compound is admixed with an aqueous solution prior to administration, wherein more preferably the aqueous solution is an isotonic aqueous solution and wherein even more preferably the isotonic aqueous solution is saline. A compound for use according to both aspects of the invention preferably is administered at least twice daily, preferably wherein the compound is administered twice daily, wherein more preferably the compound is administered twice daily in two similar or equal doses. Preferably, the interval between two administrations is at least about 1, 2, 3, 4, 5, 6, 7, 8, 9, 10, 11 or 12 hours.

A compound for use according to both aspects of the invention is preferably used to treat a subject that is a primate, more preferably the subject is a human. The subject to be treated can be a patient suffering from a mitochondrial disease or the subject can be a patient who is not suffering from a mitochondrial disease, particularly not a patient suffering from a m.3243A>G related mitochondrial disease.

DESCRIPTION OF THE INVENTION

The current invention is based on the discovery that compounds of the invention, such as amide-derivatives of 6-hydroxy-2,5,7,8-tetramethylchroman-2-carboxylic acid or 2-hydroxy-2-methyl-4-(3,5,6-trimethyl-1,4-benzoquinon-2-yl)-butanoic acid, are able to effectively suppress symptoms of a mood disorder as well as to reduce the occurrence of headaches and migraines. These effects of the compounds of the invention were first observed in the KHENERGY phase II clinical trial (www.clinicaltrials.gov: NCT 02909400) of a compound of the invention, when tested in a cross-over placebo controlled study in patients suffering from a m.3243A>G related mitochondrial disease. However, the inventors anticipate that the compounds of the invention will also suppress symptoms of a mood disorder as well as reduce the occurrence of headaches and migraines in subjects in need thereof, which subjects are not necessarily patients that suffer from a m.3243A>G related mitochondrial disease.

In a first aspect, the invention therefore concerns a method of treating, preventing or suppressing symptoms associated with a mood disorder, the method comprising administering to a subject in need thereof, an effective amount of one or more compounds of the invention as defined herein below. The effective amount is preferably an amount as defined herein below.

Alternatively, the invention pertains to a compound of the invention as defined herein below for use in treating, preventing or suppressing symptoms associated with a mood disorder, preferably by administration of an effective dose of the compound as defined herein below.

In a second aspect, the invention therefore concerns a method of treating, preventing or suppressing symptoms associated with at least one of a headache and migraine, the method comprising administering to a subject in need thereof, an effective amount of one or more compounds of the invention as defined herein below. The effective amount is preferably an amount as defined herein below.

Alternatively, the invention pertains to a compound of the invention as defined herein below for use in treating, preventing or suppressing symptoms associated with at least one of a headache and migraine, preferably by administration of an effective dose of the compound as defined herein below.

The medical use herein described is formulated as a compound as defined herein for use as a medicament for treatment of the stated condition(s) (e.g. by administration of an effective amount of the compound), but could equally be formulated as i) a method of treatment of the stated condition(s) using a compound as defined herein comprising a step of administering to a subject an effective amount of the compound, ii) a compound as defined herein for use in the manufacture of a medicament to treat the stated condition(s), wherein preferably the compound is to be administered in an effective amount, and iii) use of a compound as defined herein for the treatment of the stated condition(s), preferably by administering an effective amount. Such medical uses are all envisaged by the present invention.

The compound of the invention may be identified by general structure (I):

Herein,

T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;

L is a linker between the amide nitrogen atom and the distal nitrogen atom comprising 1 to 10 optionally substituted backbone atoms selected from carbon, nitrogen and oxygen;

N* is represented by structure (IIa) or (IIb)

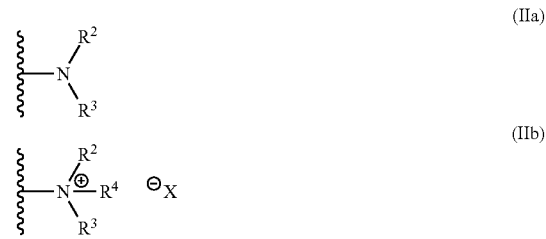

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; and $R^4$ is selected from hydrogen (H) or $C_1$-$C_6$ alkyl, wherein the alkyl moiety may be substituted with one or more halogen atoms or (halo)alkoxy moieties;

X is an anion, preferably a pharmaceutically acceptable anion.

The compound according to structure (I) comprises at least two nitrogen atoms; the nitrogen atom to which T is connected, which is also referred to as the "amide nitrogen atom", and the nitrogen atom of the N* moiety, which is also referred to as the "distal nitrogen atom". N* may be an amino moiety, when the covalent bond between the distal nitrogen atom and the adjacent backbone atom is a single bond, or part of an imine moiety, when the covalent bond between the distal nitrogen atom and adjacent backbone atom is a double bond. The distal nitrogen atom may be a neutral or a cationic. In case N* is neutral, the compound according to the invention may also be referred to by general structure (Ia). In case N* is cationic, the compound according to the invention may also be referred to by general structure (Ib).

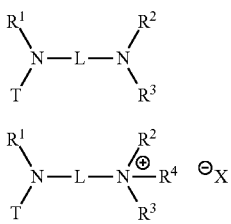

(Ia)

(Ib)

T is a water-soluble vitamin E derivative, wherein the chromanyl or chromanyl quinone framework is substituted with a carboxylic acid at the 2-position. The 2-carboxy variant of vitamin E is also known as Trolox™ (6-hydroxy-2,5,7,8-tetramethylchroman-2-carboxylic acid). Water-soluble vitamin E derivatives are known in the art and include 6-hydroxy-2,5,7,8-tetraalkyl-2-carboxy-chromanyl (general structure (IIIa), also referred to as the "closed form") and its oxidized form 2-(3-hydroxy-3-alkyl-4-oxobutyl)-3,5,6-trialkylcyclohexa-2,5-diene-1,4-dione (general structure (IIIb), also referred to as the "open form"). The inventors have found that the open form according to general structure (IIIb) is found as metabolite of the closed form according to general structure (IIIa), when the latter is administered. After 24 h treatment of a P4 cell line with compound I-IVa-X (a compound of general structure (I) wherein T is of general structure (IVa), in the S,R-configuration, and wherein as per compound X the following apply: L=L$^{19}$; R$^1$=H; R$^2$-R$^2$=L$^3$; R$^3$=H), about 48% (±10%) of closed compound was converted into the open form. About 15% (±3%) was converted during the same period when incubated in medium only. Such conversion is also disclosed in Beyrath et al., DOI: 10.1038/s41598-018-24900-3, and in Koene et al., DOI: 10.1186/s13023-017-0715-0. A preferred chromanyl framework is a 6-hydroxychromane framework. A preferred chromanyl quinone framework is a 2-(3-hydroxyalkyl)-cyclohexa-2,5-diene-1,4-dione, wherein preferably a 3-hydroxyalkyl is a 3-hydroxybutyl, more preferably a 4-oxo-3-hydroxybutyl as comprised in general structure (IIIb).

The 2-position of the closed form is the position in the oxane ring bearing the carboxylic acid (or amide, as is the case in a molecule of the invention) and an R$^7$ moiety, which is the 2-position according to naming conventions known in the art, such as IUPAC nomenclature. For the open form, the same carbon atom is intended with the 2-position, so that the carbon atom bearing the hydroxyl moiety and an R$^7$ moiety such as shown in general structure (IIIb) below is referenced. This position can also be seen as the 3-position of the alkyl moiety that is substituted to the quinone. Accordingly, T is a water-soluble vitamin E derivative, wherein the chromanyl framework is substituted with a carboxylic acid at the 2-position or wherein the chromanyl quinone framework is substituted with a carboxylic acid at the 3-position of the 3-hydroxyalkyl moiety, which is in turn substituted to the 2'position of the cyclohexa-2,5-diene-1,4-dione.

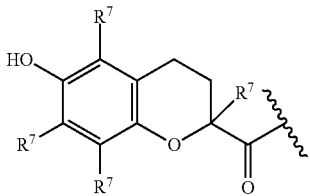

(IIIa)

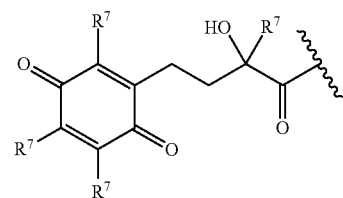

(IIIb)

Herein, each occurrence of R$^7$ is individually selected from halogen, alkyl, amino, nitro or —NHCO-alkyl. Preferred options for R$^7$ are halogen and alkyl, most preferably alkyl. In the context of R$^7$, the halogen is preferably fluorine or chlorine, most preferably chlorine. In the context of the alkyl is preferably a C$_1$-C$_6$ alkyl moiety, preferably a C$_1$-C$_6$ alkyl moiety, most preferably methyl. In the context of R$^7$, amino is preferably —NH$_2$. In the context of R$^7$, —NHCO-alkyl is preferably —NHCOMe. Preferably, each of R$^7$ is the same substituent. Most preferably, R$^7$ is methyl. In a preferred embodiment, T is represented by structure (IVa) or (IVb). In other words, structure (IVa) is a preferred embodiment of structure (IIIa), and structure (IVb) is a preferred embodiment of structure (IIIb).

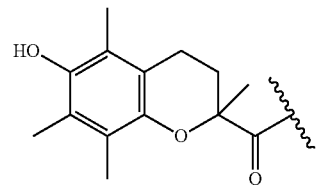

(IVa)

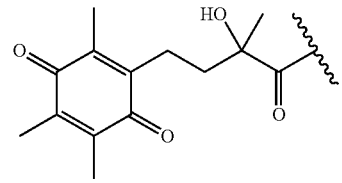

(IVb)

In a preferred embodiment, T is represented by structure IIIa or IIIb, preferably by structure IVa or IVb. In a more preferred embodiment, T is represented by structure (IIIa), preferably by structure (IVa). In an alternative preferred embodiment, T is represented by structure (IIIb), preferably by structure (IVb).

The compound identified by general structure (I) comprises at least one chiral carbon atom (stereocenter), i.e. the atom at the 2-position of T (e.g. of the oxane ring of structure (IIIa) or the butanoic acid moiety of structure (IIIa)). Both the compound having an S-configuration as the compound having an R-configuration of the carbon atom at the 2-position are encompassed in the present invention, as well as mixtures of the different stereoisomers. Such a mixture may have one of the configurations in enantiomeric excess, or may be racemic. Whenever one or more additional stereocenters are present in the compound according to the invention, for example in linker L, each may individually exist in the S-configuration, in the R-configuration, or as a mixture of both configurations. Such a mixture may have one of the configurations in enantiomeric excess, or may be racemic. In case addition stereocenters are present, all diastereomers of the compound of general structure (I), in each possible ratio, are encompassed in the present invention.

In a preferred embodiment, the solubility of the compound of the invention in water, expressed as $\log(P_{ow})$ is between 2.0 and 5.0, preferably between 2.5 and 4.5, more preferably between 3.0 and 4.0. $\log(P_{ow})$, the logarithm of the partition coefficient between 1-octanol and water, is a well-known measure of water solubility. Compounds having a $\log(P_{ow})$ value between 3 and 4 are ideally balanced between sufficient water solubility for preparation of aqueous solutions or suspensions and sufficient lipophilicity to ensure efficient transport of the compound over the cellular membrane. The skilled person will appreciate how to determine which combinations of L, $R^1$, $R^2$, $R^3$, $R^4$ and X as defined herein to afford a compound having a $\log(P_{ow})$ value between 3 and 4. Suitable tests to define the $\log(P_{ow})$ value of a compound are well-known to the skilled person, and include but are not limited to the shake-flask method, ITIES, the droplet method or using HPLC. The $\log(P_{ow})$ of a compound can also be predicted using QSPR algorithms.

$R^1$ and $R^2$ are each independently selected from hydrogen (H), $C_1$-$C_6$ alkyl or $C_1$-$C_6$ alkenyl, or one or both of $R^1$ and $R^2$ are embedded in a cyclic structure as described here below. Preferably, $R^1$ is H or $C_1$-$C_2$ alkyl or $R^1$ and $R^2$ are joined together and thus form a second linker between the amide nitrogen atom and the distal nitrogen atom, or $R^1$ is joined with a backbone atom of the linker L in a cyclic structure, more preferably $R^1$ is H or $C_1$-$C_2$ alkyl, even more preferably $R^1$ is H or methyl (Me), most preferably $R^1$ is H. Preferably, $R^2$ is H or $C_1$-$C_2$ alkyl or $R^1$ and $R^2$ are joined together and thus form a second linker between the amide nitrogen atom and the distal nitrogen atom, or $R^2$ is joined with a backbone atom of the linker L in a cyclic structure, more preferably $R^2$ is H, $C_1$-$C_2$ alkyl or joined with a backbone atom of the linker L in a cyclic structure, even more preferably $R^2$ is H, methyl (Me) or joined with a backbone atom of the linker L in a cyclic structure. In one embodiment, $R^2$ is H, methyl (Me), preferably $R^2$ is H. In an especially preferred embodiment, $R^2$ is joined with a backbone atom of the linker L in a cyclic structure, as further defined below, preferably a saturated cyclic structure, most preferably a piperidine ring.

In one embodiment, the amide nitrogen atom is connected to the distal nitrogen atom via a second linker. This second linker is defined by joining together $R^1$ on the amide nitrogen atom and $R^2$ on the distal nitrogen atom. Thus, the amide nitrogen atom, the distal nitrogen atom, the first linker and the second linker together form a cyclic structure, preferably a 4-10-membered cyclic structure, more preferably a 5-8-membered cyclic structure, most preferably a 6-membered cyclic structure. In a preferred embodiment, the second linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the distal nitrogen atom.

In another embodiment, the amide nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{1'}$, which is joined together with $R^1$ on the amide nitrogen atom. Thus, the amide nitrogen atom, part of first linker located between the amide nitrogen atom and the atom bearing $R^{1'}$, the backbone atom bearing $R^{1'}$ and the second linker together form the cyclic structure. In this embodiment, the distal nitrogen atom is not included in this cyclic structure, but instead only part of the backbone of the linker is included. In a preferred embodiment, this connection between the amide nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the amide nitrogen atom and the backbone atom of the linker. Most preferably, the cyclic structure containing the amide nitrogen atom is a fully saturated ring, preferably selected from a piperidine ring, a pyrrolidine ring, a piperazine ring, an imidazolidine ring, a pyrazolidine ring and an azepane ring, more preferably a piperazine ring, a piperidine ring or a pyrrolidine ring, most preferably a piperidine ring.

In another embodiment, the distal nitrogen atom is connected to a backbone atom of the linker via a second linker, thereby forming a cyclic structure, preferably a 4-10-membered cyclic structure, more preferably a 5-8-membered cyclic structure, most preferably a 6-membered cyclic structure. The backbone atom of the linker to which the nitrogen atom is connected in this respect has a substituent $R^{2'}$, which is joined together with $R^2$ on the distal nitrogen atom. Thus, the distal nitrogen atom, part of first linker located between the distal nitrogen atom and the atom bearing $R^{2'}$, the backbone atom bearing $R^{2'}$ and the second linker together form the cyclic structure. In this embodiment, the amide nitrogen atom is not included in this cyclic structure, but instead only part of the backbone of the linker is included. In a preferred embodiment, this connection between the distal nitrogen atom and a backbone atom of the linker is a —$CH_2$—$CH_2$— or —$CH_2$—$CH_2$—$CH_2$— bridge, most preferably a —$CH_2$—$CH_2$— bridge, wherein two or three, preferably two, carbon atoms are present between the distal nitrogen atom and the backbone atom of the linker. Most preferably, the cyclic structure containing the distal nitrogen atom is a fully saturated ring, preferably selected from a piperidine ring, a pyrrolidine ring, a piperazine ring, an imidazolidine ring, a pyrazolidine ring and an azepane ring, more preferably a piperidine ring or a pyrrolidine ring, most preferably a piperidine ring. It is also possible that a connection exists between $R^1$ on the amide nitrogen atom and an $R^{1'}$ substituent on the linker and between $R^2$ on the distal nitrogen atom and an $R^{2'}$ substituent on the linker.

In another embodiment, the distal nitrogen atom is connected to a backbone atom of the linker via a second and a third linker, thereby forming a bicyclic structure, preferably a 6-12-membered cyclic structure, more preferably a 6-9-membered cyclic structure such as a bicyclooctane-like structure, most preferably a [2.2.2]bicyclooctane-like structure. The backbone atom of the linker to which the nitrogen atom is connected in this respect has a substituent $R^{2'}$ and $R^{3'}$ which are joined together with $R^2$ and $R^3$, respectively, on the distal nitrogen atom. Thus, the distal nitrogen atom, part of first linker located between the distal nitrogen atom and the atom bearing $R^{2'}$, the backbone atom bearing $R^{2'}$ and the second linker together form one cycle of the bicyclic structure, and the part of the first linker located between the distal nitrogen atom and the atom bearing R3', and the third linker form a second cycle of the bicyclic structure. In this embodiment, the amide nitrogen atom is not included in this bicyclic structure, but instead only part of the backbone of the linker is included. In a preferred embodiment, this connection between the distal nitrogen atom and a backbone atom of the linker is a —$CH_2$—, —$CH_2$—$CH_2$— or —$CH_2$—$CH_2$—$CH_2$— bridge, most preferably a —$CH_2$—$CH_2$— bridge, wherein two or three, preferably two, carbon atoms are present between the distal nitrogen atom and the backbone atom of the linker. Most preferably, the cyclic structure containing the distal nitrogen atom is a fully saturated structure.

Among the above-mentioned possibilities for $R^2$, it is most preferred that the distal nitrogen atom is connected to a backbone atom of the linker via a second linker wherein $R^2$ is joined with $R^{2'}$, as further defined here above.

When the distal nitrogen atom is part of an imine moiety, the linker L comprises at least one double bond located between the distal nitrogen atom and the adjacent backbone atom of the linker, or $R^2$ comprises at least one double bond located between the distal nitrogen atom and the adjacent atom of $R^2$ (i.e. $R^2=C_1-C_6$ alkenyl). In such instances, $R^3$ is absent. In case the distal nitrogen atom is part of an imine moiety, wherein a double bond is located between the distal nitrogen atom and the adjacent backbone atom of the linker, the compound of the invention may be represented by structure (Ic).

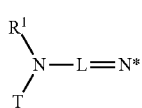

(Ic)

When the distal nitrogen atom is part of an imine moiety is in structure (Ic), it may either be cationic or neutral. The same options for N* as defined by structures (IIa) and (IIb), wherein $R^3$ is absent, apply. In case the distal nitrogen atom is neutral and part of an imine moiety, wherein a double bond is located between the distal nitrogen atom and the adjacent backbone atom of the linker, the compound according to the invention may also be referred to by general structure (Id). In case the distal nitrogen atom is cationic and part of an imine moiety, wherein a double bond is located between the distal nitrogen atom and the adjacent backbone atom of the linker, the compound according to the invention may also be referred to by general structure (Ie).

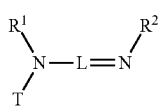

(Id)

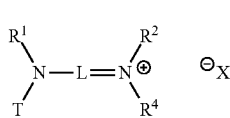

(Ie)

In the context of the present invention, the distal nitrogen being part of an imine moiety includes instances wherein the distal nitrogen atom is part of an heteroaromatic ring, in particular a pyrrole ring, a pyridine ring or a imidazole ring, in which instances a double bond is formally present between the distal nitrogen atom and the adjacent carbon atom either in the linker or in $R^2$. Preferred moieties comprising an imine moiety include guanidine, amidine and pyridine. For guanidine and amidine, one of the nitrogen atoms is substituted to form the connection with the amide nitrogen atom via linker L. For pyridine, one of the carbon atoms is substituted. When the distal nitrogen atom is part of an amine moiety, it is connected to the linker and $R^2$ via two single bonds, and $R^3$ is present. It is preferred that the distal nitrogen atom is part of an amine moiety, i.e. having three or four single bonds to each of $R^1$, $R^2$, $R^3$ and optionally $R^4$.

In the instance that $R^3$ is present, $R^3$ is selected from hydrogen (H), $C_1-C_6$ alkyl or $C_1-C_6$ alkenyl, wherein the alkyl or alkenyl moiety may be substituted with one or more halogen atoms, hydroxyl groups or (halo)alkoxy moieties, preferably $R^3$ is H, $C_1-C_6$ alkyl, more preferably $R^3$ is H or $C_1-C_4$ alkyl, even more preferably $R^3$ is H or $C_1-C_2$ alkyl, wherein the alkyl moiety may be substituted with one or more halogen atoms, hydroxyl groups or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Preferred substituents for the alkyl moieties are halogen atoms and alkoxy moieties. Suitable moieties for $R^3$ include, preferably are limited to, H, methyl (Me), trifluoromethyl (—$CF_3$), ethyl (Et), isopropyl (iPr), cyclopropyl (-cPr), methylene cyclopropyl (—$CH_2cPr$), n-propyl (n-Pr), 2,2,2-trifluoroethyl (—$CH_2CF_3$), 2-hydroxy-ethyl (—$CH_2CH_2OH$), and methoxymethyl (—$CH_2OCH_3$), more preferably $R^3$ is H or methyl (Me), most preferably $R^3$ is H. Alternatively, $R^3$ is preferably $C_1-C_4$ alkyl, wherein the alkyl moiety may be substituted with one or more halogen atoms or (halo)alkoxy moieties, more preferably $R^3$ is $C_1-C_2$ alkyl, wherein the alkyl moiety may be substituted with one or more halogen atoms or (halo)alkoxy moieties.

In case the distal nitrogen atom is in cationic form, it formally originates from protonation or alkylation, preferably protonation or methylation of a trivalent nitrogen atom. The trivalent nitrogen atom is preferably an amine moiety, either primary, secondary or tertiary, or an imine moiety, either primary or secondary. The counter ion (X) of the cationic distal nitrogen atom is a negatively charged ion, preferably a monovalent negatively charged ion, more preferably an anion as indicated herein below. The synthesis of the compounds of the invention does not need to encompass the protonation or alkylation of an amine or imine nitrogen atom. The cationic distal nitrogen atom may also be formed via a different route. As such, the cationic distal nitrogen atom only "formally" originates from the protonation or alkylation of an amine or imine nitrogen atom.

$R^4$ is the substituent on the cationic distal nitrogen atom, which originates from formal protonation or alkylation of the amine or imine moiety. Thus, the compound according to this embodiment, in view of the presence of the cationic nitrogen atom and X, is a salt, preferably a pharmaceutically acceptable salt. Pharmaceutically acceptable salts are those salts that are suitable to be administered as drugs or pharmaceuticals to humans and/or animals. The pharmaceutically acceptable salts of the amine or imine moiety of the compound according to the invention are known to those skilled in the art, and originate from formal treatment of the compound with an acid (protonation agent) or an alkylating agent. Suitable acids include organic acids or inorganic acids. Examples of inorganic acids include, but are not limited to, hydrochloric acid (HCl), hydrobromic acid (HBr), hydroiodic acid (HI), sulphuric acid ($H_2SO_4$), nitric acid ($HNO_3$), trifluoroacetic acid (TFAH or $CF_3CO_2H$) and phosphoric acid ($H_3PO_4$). Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids and salicylic acid. When an acid as exemplified here is used to formally prepare the salt, $R^4$ is hydrogen, and the type of acid determines counter ion X. Alternatively, the salt can be formed by formal treatment with an alkylating agent. Suitable alkylating agents include, but are not limited to, $C_1$-$C_6$ alkyl halides (such as methyl iodide, ethyl iodide, propyl iodide, butyl chloride, butyl fluoride, butyl bromide), dimethyl sulphate, dimethyl carbonate, methyl triflate, methyl fluorosulfonate, methyl chlorosulfonate, methyl methanesulfonate and methyl benzenesulfonate. The salt may be prepared by actual treatment of the non-salt compound with an acid or alkylation agent, as indicated above, or via other means known in the art and/or exemplified further below.

$R^4$ is selected from hydrogen (H) or $C_1$-$C_6$ alkyl, wherein the alkyl moiety may be substituted with one or more halogen atoms or (halo)alkoxy moieties, preferably $R^4$ is H or $C_1$-$C_4$ alkyl, wherein the alkyl moiety may be substituted with one or more halogen atoms or (halo)alkoxy moieties, more preferably $R^4$ is H or $C_1$-$C_2$ alkyl, wherein the alkyl moiety may be substituted with one or more halogen atoms or (halo)alkoxy moieties. Halogen atoms include fluorine (F), chlorine (Cl), bromine (Br), iodine (I), and astatine (At), preferably the halogen atom is fluorine (F). Preferred alkoxy moieties include methoxy and ethoxy. In haloalkoxy moieties, at least one hydrogen atom of an alkoxy moiety is replaced by a halogen atom, preferably by F. Suitable moieties for $R^4$ include, preferably are limited to, H, methyl (Me), trifluoromethyl (—$CF_3$), ethyl (Et), isopropyl (iPr), cyclopropyl (-cPr), methylene cyclopropyl (—$CH_2$cPr), n-propyl (n-Pr), 2,2,2-trifluoroethyl (—$CH_2CF_3$), methoxymethyl (—$CH_2OCH_3$). Even more preferably $R^4$ is H or methyl (Me), most preferably $R^4$ is H.

X can be any anion, preferably a physiologically or pharmaceutically acceptable anion, more preferably a monovalent anion. X is preferably selected from F, Cl, Br, I, $HSO_4$, $NO_3$, TFA ($CF_3CO_2$), formate, acetate, propionate, glycolate, pyruvate, oxalate, maleate, malonate, succinate, fumarate, tartarate, citrate, benzoate, cinnamate, mandelate, sulfonate and salicylate. Preferably, X is Cl, I, TFA or formate, more preferably Cl, I, TFA or formate, even more preferably X is Cl or formate, most preferably X is Cl. When the cationic nitrogen atom originates from formal protonation, this protonation is preferably accomplished with hydrogen chloride (HCl), trifluoroacetic acid (TFAH or $CF_3CO_2H$) or formic acid (HCOOH), more preferably with HCl or formic acid. Formal methylation is preferably accomplished with methyl iodide (MeI). Thus, in a preferred embodiment, $R^4$=Me when X=$I^-$, and $R^4$=H when X=$Cl^-$, $TFA^-$ or formate.

Appropriate linkers L to connect the amide nitrogen atom to the distal nitrogen atom are linkers preferably comprising 1 to 10 optionally substituted backbone atoms more preferably comprising 1 to 8 optionally substituted backbone atoms. L may thus comprise 1, 2, 3, 4, 5, 6, 7, 8, 9 or 10 optionally substituted backbone atoms. It is preferred that linker L comprises 1 to 10 optionally substituted backbone atoms selected from carbon, nitrogen and oxygen. Herein, backbone atoms are those atoms that make up the shortest chain between the amide nitrogen atom and the distal nitrogen atom. The backbone may be a linear structure, but (part of) the backbone may also be part of a cyclic structure. When the backbone is part a cyclic structure, the backbone is defined as the shortest chain between the amide nitrogen atom and the distal nitrogen atom. In one embodiment, one of the backbone atoms comprises a substituent $R^5$, and one of the backbone atoms comprises a substituent $R^{5'}$, preferably two different backbone atoms comprise the substituents $R^5$ and $R^{5'}$, wherein $R^5$ and $R^{5'}$ are joined to form a cyclic structure, preferably a 4-10-membered cyclic structure, more preferably a 5-8-membered cyclic structure, most preferably a 6-membered cyclic structure. In this embodiment, the amide nitrogen atom and the distal nitrogen atom are not included in the cyclic structure, but instead only part of the backbone of the linker is included. In a preferred embodiment, this connection between the backbone atom(s) of the linker, bearing the $R^5$ and $R^{5'}$ substituents, is a —$(CH_2)_n$— bridge, wherein n=1-6, preferably a —$CH_2$—$CH_2$— or —$CH_2$—$CH_2$—$CH_2$— bridge, wherein one to six, preferably two or three, carbon atoms are present between the substituted backbone atom(s) of the linker.

In a preferred embodiment, the backbone atoms are selected from carbon, nitrogen and oxygen, preferably from carbon and nitrogen. Such a backbone according to this preferred embodiment may be identified as $C_{n-m}N_m$, wherein n designates the total number of atoms in the backbone, and m the number of nitrogen atoms in the backbone. Each of n and m is a non-negative integer. Suitable linkers have n=1-10 and m=0-4, preferably n=2-7 and m=0-3, more preferably n=4-7 and m=0-2. Especially preferred linkers have a backbone identified as $C_{n-m}N_m$, wherein n=2 and m=0 ($C_2$); n=5 and m=1 ($C_4N$); n=3 and m=0 ($C_3$); n=4 and m=1 ($C_3N$); n=7 and m=2 ($C_5N_2$); n=4 and m=0 ($C_4$); n=6 and m=1 ($C_5N$); or n=5 and m=0 ($C_5$). Most preferably, all backbone atoms are carbon atoms (m=0).

To fulfill their valence requirements, the carbon and nitrogen backbone atoms of the linker may bear hydrogen atoms, may be substituted, or double or triple bonds may be present between adjacent backbone atoms, as will be understood by the skilled person. In the context of the invention, hydrogen is not regarded a substituent. Whenever an oxygen atom is present as backbone atom in the linker, the skilled person will understand that the oxygen backbone atom bears no hydrogen atoms, substituents or double or triple bonds. Triple bonds may be present between two carbon atoms of the backbone. The backbone atoms, together with the hydrogen atoms and/or the substituents, constitute the linker. In the context of the present invention, "optionally substituted" is used to indicate that an (backbone) atom may bear one or more substituents, or may bear no substituents and sufficient hydrogen atoms may be present instead, to fulfill the valence requirements of said (backbone) atom.

Suitable substituents include but are not limited to halogen, $NH_2$, $NHR^6$, $N(R^6)_2$, $NHNH_2$, $N_3$, NHC(=O)$R^6$, NHC(=O)$NHR^6$, NHC(=O)$NH_2$, NHC(=O)$OR^6$, OH, $OR^6$, OC(=O)$R^6$, $R^6$ (e.g. alkyl, cycloalkyl), aralkyl, alkenyl, alkynyl, aryl, heteroaryl, OC(=O)$OR^6$, OC(=O)$NHR^6$, O($SO_2$)$R^6$, O($SO_2$)OH, O($PO_2$)OH, SH, $SR^6$, C(=O)$R^6$, alkyl-$NH_2$, alkyl-OH, alkyl-SH, C(=O)$CF_3$, C(=O)$OR^6$, C(=O)OH, C(=O)H, C(=O)$OR^6$, C(=O)$NH_2$, C(=O)$NMe_2$, C(=O)N$(R^6)_2$, C(=S)$NH_2$ C(=S)SH, CN, NC, CNO, ONC, OCN, SCN, SNC, CNS, S(=O)$R^6$, S(=O)$_2R^6$, S(=O)$_2$(OH), P(=O)(OH)$_2$ or P(=O)(OH)($OR^6$). Atoms having two or more remaining valencies, such as carbon backbone atoms, may bear a double bonded substituent, such as oxo (=O), imino (=NH or =$NR^6$), thioxo (=S), alkylidene (=$CH_2$ or =$CHR^6$ or =$C(R^6)_2$). Herein, each $R^6$ is independently an alkyl moiety, preferably a $C_1$-$C_6$ alkyl moiety, more preferably a $C_1$-$C_2$ alkyl moiety. Within $R^6$, one or more $CH_2$ moieties may each independently be replaced by one of O, S or NH, and/or one or more CH moieties may be replaced by N. In addition, two substituents on the same atom or on different atoms may be joined to form cyclic structures. If two substituents on a single backbone atom are joined in a cyclic structure, this cyclic structure may be regarded as being connected via a spiro junction to the backbone. If two substituents on different backbone atoms are joined in a cyclic structure, part of this cyclic structure is (part of) the backbone, and the backbone is considered to be the shortest chain of atoms between the amide nitrogen atom and the distal nitrogen atom. The cyclic structures formed as such may be all-carbon or may comprise 0-3 heteroatoms (e.g. N, O, S and/or P), and may comprise 0-3 double bonds. All atoms in these cyclic structures may optionally be substituted. Examples of suitable cyclic structures are optionally substituted cycloalkyl, optionally substituted cycloheteroalkyl, optionally substituted aryl or optionally substituted heteroaryl. As further indicated below, a cyclic structure may also be formed by joining one substituent on a backbone atom with $R^1$ on the amide nitrogen atom or with $R^2$ on the distal nitrogen atom.

In the context of the present invention, the term "alkyl" refers to saturated aliphatic groups including straight-chain, branched-chain, cyclic groups, and combinations thereof, having the number of carbon atoms specified, or if no number is specified, preferably having up to 12 carbon atoms. "Straight-chain alkyl" or "linear alkyl" group refers to alkyl groups that are neither cyclic nor branched, commonly designated as "n-alkyl" groups. One subset of alkyl groups is $C_1$-$C_6$ alkyl, which includes groups such as methyl, ethyl, n-propyl, isopropyl, butyl, n-butyl, isobutyl, sec-butyl, t-butyl, pentyl, n-pentyl, hexyl, cyclopropyl, cyclobutyl, cyclopentyl, cyclohexyl, and any other alkyl group containing between one and six carbon atoms, where the $C_1$-$C_6$ alkyl groups can be attached via any valence on the $C_1$-$C_6$ alkyl groups.

In one embodiment, the backbone atoms are optionally substituted with one or more substituents selected from the group consisting of $R^6$, carboxy, oxo, and primary amino or a backbone atom may be joined with $R^1$ to form a 4-10-membered cyclic structure and/or a backbone atom may be joined with $R^2$ to form a 4-10-membered cyclic structure, or two backbone atoms may be joined to form a cyclic structure, wherein $R^6$ is as defined above, preferably $R^6$ is $C_1$-$C_6$ alkyl, more preferably $C_1$-$C_2$ alkyl. Preferred substituents of the backbone atoms are alkyl, such as methyl (Me or —$CH_3$), carboxyl (—C(=O)OH), oxo (=O) and primary amino (—$NH_2$).

Preferred linkers L are identified here below as $L^1$ to $L^{28}$. More preferred are $L^1$ to $L^{26}$:

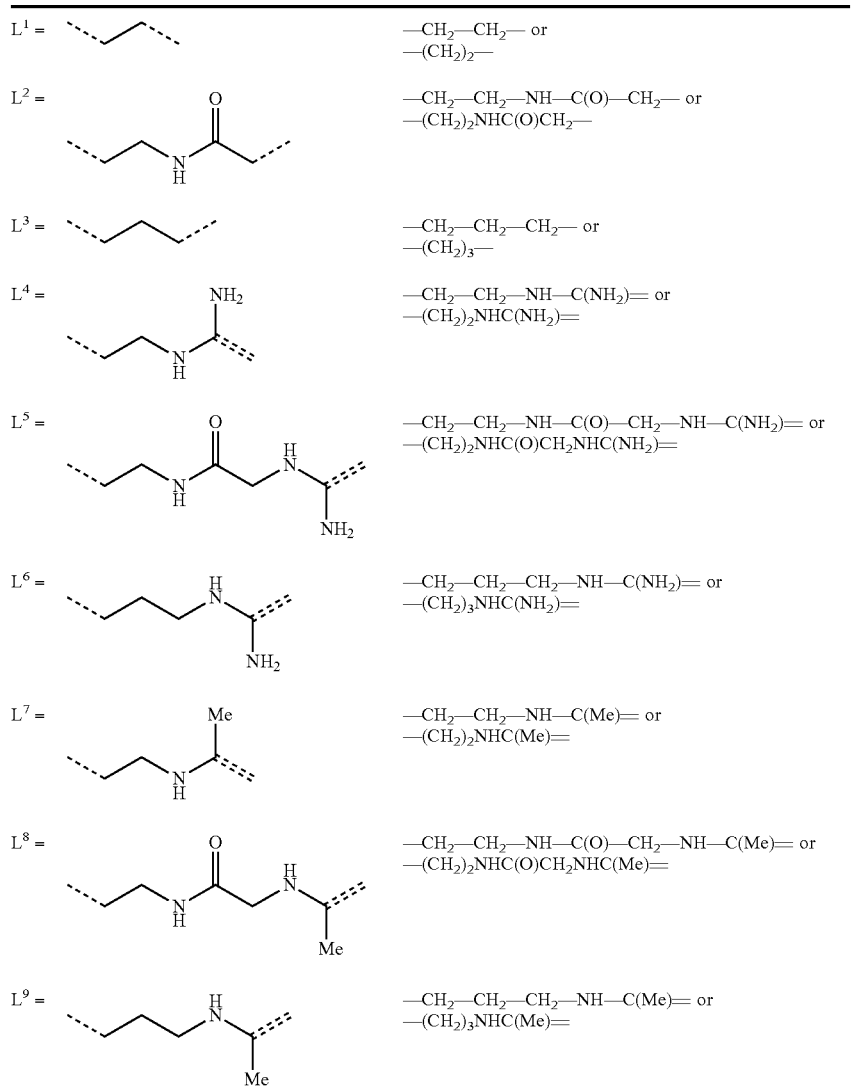

-continued

| | | |
|---|---|---|
| L$^{10}$ = | 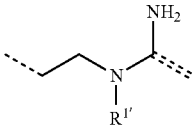 | —CH$_2$—CH$_2$—NR$^{1'}$—C(NH$_2$)= or<br>—(CH$_2$)$_2$NR$^{1'}$C(NH$_2$)= |
| L$^{11}$ = | 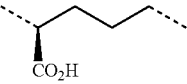 | —C(CO$_2$H)—CH$_2$—CH$_2$—CH$_2$— or<br>—C(CO$_2$H)(CH$_2$)$_3$— |
| L$^{12}$ = | 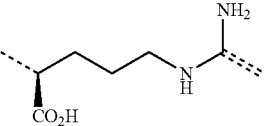 | —C(CO$_2$H)—CH$_2$—CH$_2$—CH$_2$—NH—C(NH$_2$)= or<br>—C(CO$_2$H)(CH$_2$)$_3$NHC(NH$_2$)= |
| L$^{13}$ = | 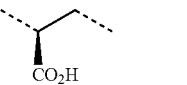 | —C(CO$_2$H)—CH$_2$— or<br>—C(CO$_2$H)CH$_2$— |
| L$^{14}$ = | 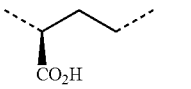 | —C(CO$_2$H)—CH$_2$—CH$_2$— or<br>—C(CO$_2$H)(CH$_2$)$_2$— |
| L$^{15}$ = | 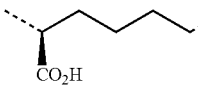 | —C(CO$_2$H)—CH$_2$—CH$_2$—CH$_2$—CH$_2$— or<br>—C(CO$_2$H)(CH$_2$)$_4$— |
| L$^{16}$ = | 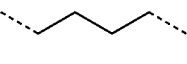 | —CH$_2$—CH$_2$—CH$_2$—CH$_2$— or<br>—(CH$_2$)$_4$— |
| L$^{17}$ = | 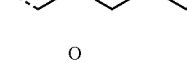 | —CH$_2$—CH$_2$—CH$_2$—CH$_2$—CH$_2$— or<br>—(CH$_2$)$_5$— |
| L$^{18}$ = | 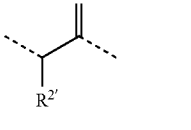 | —CHR$^{2'}$—C(O)— or<br>—CHR$^{2'}$C(O)— |
| L$^{19}$ = | 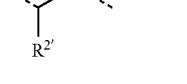 | —CHR$^{2'}$—CH$_2$— or<br>—CHR$^{2'}$CH$_2$— |
| L$^{20}$ = | 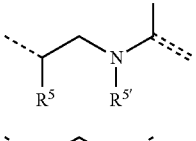 | —CHR$^5$—CH$_2$—NR$^{5'}$—C(Me)= or<br>—CHR$^5$CH$_2$NR$^{5'}$C(Me)= |
| L$^{21}$ = | 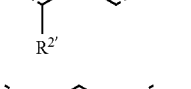 | —CHR$^{2'}$—CH$_2$—CH$_2$— or<br>—CHR$^{2'}$(CH$_2$)$_2$— |
| L$^{22}$ = | 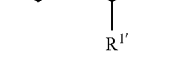 | —CH$_2$—CH$_2$—CHR$^{1'}$— or<br>—(CH$_2$)$_2$CHR$^{1'}$— |
| L$^{23}$ = | 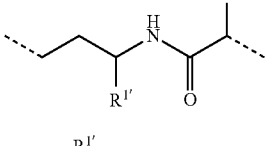 | —CH$_2$—CH$_2$—CHR$^{1'}$—NH—C(O)—C(Me)— or<br>—(CH$_2$)$_2$CHR$^{1'}$NHC(O)C(Me)— |
| L$^{24}$ = | 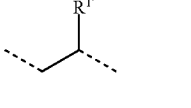 | —CH$_2$—CHR$^{1'}$— or<br>—CH$_2$CHR$^{1'}$— |

-continued

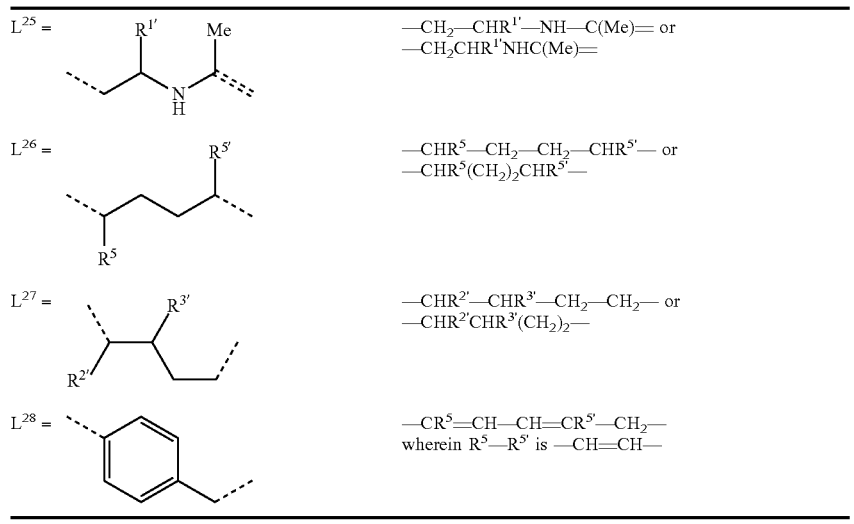

| | | |
|---|---|---|
| $L^{25}$ = | (structure with R¹', Me, NH) | —CH₂—CHR¹'—NH—C(Me)= or<br>—CH₂CHR¹'NHC(Me)= |
| $L^{26}$ = | (structure with R⁵', R⁵) | —CHR⁵—CH₂—CH₂—CHR⁵'— or<br>—CHR⁵(CH₂)₂CHR⁵'— |
| $L^{27}$ = | (structure with R³', R²') | —CHR²'—CHR³'—CH₂—CH₂— or<br>—CHR²'CHR³'(CH₂)₂— |
| $L^{28}$ = | (phenyl structure) | —CR⁵=CH—CH=CR⁵'—CH₂—<br>wherein R⁵—R⁵' is —CH=CH— |

Herein, it is preferred that the dashed bond at the left side of each of the structures for $L^1$ to $L^{28}$ indicates the bond between the linker and the amide nitrogen atom, and the dashed bond at the right side of each of the structures for $L^1$ to $L^{28}$ indicates the bond between the linker and the distal nitrogen atom.

Each occurrence of $R^{1'}$ represents the connection of a second linker between the linker and the amide nitrogen atom, wherein $R^{1'}$ is joined with $R^1$ via the second linker, thus forming a 4-10-membered cyclic structure, preferably a 5-8-membered cyclic structure, most preferably a 6-membered cyclic structure, which is built up from the amide nitrogen atom, 1-4 atoms of the backbone of the linker, and 1-4 atoms which make up the bridge joining $R^1$ and $R^{1'}$. Likewise, each occurrence of $R^{2'}$ represents the connection of a second linker between the linker and the cationic nitrogen atom, wherein $R^{2'}$ is joined with $R^2$ via the second linker, thus forming a 4-10-membered cyclic structure, preferably a 5-8-membered cyclic structure, most preferably a 6-membered cyclic structure, which is built up from the cationic nitrogen atom, 1-4 atoms of the backbone of the linker, and 1-4 atoms which make up the bridge joining $R^2$ and $R^{2'}$. Likewise, each occurrence of $R^5$ and $R^{5'}$ represent the connection of a second linker between one backbone atom of the linker, bearing $R^5$, and another backbone atom of the linker, bearing $R^{5'}$, wherein $R^{5'}$ is joined with $R^5$ via the second linker, thus forming a 4-10-membered cyclic structure, preferably a 5-8-membered cyclic structure, most preferably a 6-membered cyclic structure, which is built up from 2-5 atoms of the backbone of the linker, and 1-5 atoms which make up the bridge joining $R^5$ and $R^{5'}$. Thus, in linkers $L^{10}$, $L^{22}$, $L^{23}$, $L^{24}$ and $L^{25}$, $R^{1'}$ is joined to $R^1$ via a second linker, preferably a —CH₂—CH₂— or —CH₂—CH₂—CH₂— bridge, more preferably a —CH₂—CH₂— bridge. Thus, in a compound comprising linker $L^{10}$, wherein $R^{1'}$ and $R^1$ are joined via a —CH₂—CH₂— bridge, the amide nitrogen atom is embedded in a six-membered cyclic structure, which is built up from the amide nitrogen atom, two carbon atoms and one nitrogen atom of the backbone of the linker, and two carbon atoms which make up the bridge of $R^1$ and $R^{1'}$. This —CH₂—CH₂— bridge between the amide nitrogen atom and the central nitrogen atom in the backbone of linker $L^{10}$ may be represented as $L^1$. Likewise, in linkers $L^{18}$, $L^{19}$ and $L^{21}$, $R^{2'}$ is joined to $R^2$ via a second linker, preferably a —CH₂—CH₂— or —CH₂—CH₂—CH₂— bridge, more preferably a —CH₂—CH₂—CH₂— bridge. Likewise, in linker $L^{20}$ and $L^{26}$, $R^{5'}$ is joined to $R^5$ via a second linker, preferably a —CH₂—CH₂— or —CH₂—CH₂—CH₂— bridge, more preferably a —CH₂—CH₂— bridge.

Linker $L^{26}$ comprises a disubstituted cycloalkyl moiety, preferably a disubstituted cyclohexyl moiety, and may thus occur in either the cis-form or the trans-form, preferably in the trans-form.

Linker $L^{27}$ comprises a bicyclic cycloalkyl moiety, preferably a bicyclic cyclooctyl moiety. When L=$L^{27}$ it is highly preferred that L, $R^2$, and $R^3$ together comprise 7, 8, 9, 10, 11, or 12 carbon atoms. Most preferably L27 is comprised in an azabicyclooctane such as azabicyclo[2.2.2]octane.

Linkers $L^{11}$, $L^{12}$, $L^{13}$, $L^{14}$, $L^{15}$, $L^{18}$ (as long as $R^2$-$R^{2'}$ is not —C(O)—), $L^{19}$ (as long as $R^2$-$R^{2'}$ is not —CH₂—), $L^{20}$ (as long as $R^5$-$R^{5'}$ is not —CH₂—), $L^{21}$ (as long as $R^2$-$R^{2'}$ is not —CH₂—CH₂—), $L^{22}$ (as long as $R^1$-$R^{1'}$ is not —CH₂—CH₂—), $L^{23}$ (as long as $R^1$-$R^{1'}$ is not —CH₂—CH₂—), $L^{24}$ (as long as $R^1$-$R^{1'}$ is not —CH₂—) and $L^{25}$ (as long as $R^1$-$R^{1'}$ is not —CH₂—) comprise an additional stereocenter. The stereoisomer, when indicated in the structures of those linkers, above is meant as illustrative, not as limiting. As indicated further above, each stereocenter present in the compounds according to the invention may individually be present in each of its stereoisomeric forms, either S or R, or as a mixture of both isomers in any ratio. In view of the stereocenter already present at the 2-position of T, the compounds having these linkers may be (R,R); (S,R); (R,S); or (S,S). Throughout the description, the first designator (R or S) of the configuration is for the 2-position of T, and the second designator thereof defines the configuration of the additional stereocenter that may be present in the compound according to the invention. For $L^{23}$ the methyl group as indicated by "Me" in the table above is preferably (S).

In preferred embodiments linkers are Especially preferred linkers are $L^5$, $L^8$, $L^{11}$, $L^{12}$, $L^{16}$, $L^{17}$, $L^{19}$, $L^{21}$, $L^{26}$, $L^{27}$, and $L^{28}$. Especially preferred linkers are $L^5$, $L^8$, $L^{11}$, $L^{12}$, $L^{16}$, $L^{17}$, $L^{19}$, $L^{21}$ and $L^{26}$. Even more preferred linkers are $L^{11}$, $L^{16}$, $L^{19}$ and $L^{26}$, and most preferably the linker is $L^{19}$. Preferably, $L^{19}$ is combined with $R^2$-$R^{2'}$=$L^1$ or $L^3$, most preferably with $R^2$-$R^{2'}$=$L^3$. Preferably, $L^{21}$ is combined with $R^2$-$R^{2'}$=$L^1$ or $L^3$, most preferably with $R^2$-$R^{2'}$=$L^1$. Preferably, $L^{26}$ is combined with $R^5\text{-}R^{5'}\text{=}L^1$ or $L^3$, more preferably with $R^5\text{-}R^{5'}\text{=}L^1$, most preferably wherein the cyclohexyl is trans-1,4-disubstituted. Especially preferred is the combination of linker $L^{19}$ with $R^2\text{-}R^{2'}\text{=}L^3$ and $R^3$=H, Me, Et, iPr, $CH_2OCH_3$ or $CH_2CF_3$, more preferably $R^3$=Me, Et, iPr or $CH_2CF_3$, most preferably $R^3$=H.

In case N* is according to structure (IIa), it is preferred that linker L contains 1-5 optionally substituted backbone atoms and/or linker L contains at least one backbone atom other than carbon. In case N* is according to structure (IIa), it is especially preferred that the distal nitrogen atom is connected to a backbone atom of the linker via a second linker wherein $R^2$ is joined with $R^{2'}$, more preferably wherein the cyclic structure thus formed is a piperidine ring, a pyrrolidine ring, an imidazolidine ring, a pyrazolidine ring or an azepane ring, most preferably a piperidine ring, and/or at least one of the backbone atoms is substituted with a carboxylic acid moiety. In case N* is according to structure (IIa), it is preferred that L is any one of $L^2$, $L^4\text{-}L^{21}$, $L^{23}$, $L^{25}$, $L^{26}$, $L^{27}$, and $L^{28}$, especially preferred that L is any one of $L^2$, $L^4\text{-}L^{21}$, $L^{23}$, $L^{25}$ and $L^{26}$, more preferably one of $L^5$, $L^8$, $L^{11}$, $L^{12}$, $L^{16}$, $L^{17}$, $L^{19}$, $L^{21}$ and $L^{26}$. In case N* is according to structure (IIb), it is preferred that $R^4$ is H or Me, more preferably $R^4$ is H, and X is Cl, I, TFA or formate, even more preferably X is Cl or formate, most preferably X is Cl. In case N* is according to structure (IIb), it is preferred that linker L contains 3-10 backbone atoms, or 2 backbone atoms of which one is connected to the distal nitrogen atom via a second linker. In case N* is according to structure (IIb), it is preferred that L is any one of $L^2$, $L^4\text{-}L^{21}$, $L^{23}$, $L^{25}$, $L^{26}$, $L^{27}$, and $L^{28}$, especially preferred that L is any one of $L^2\text{-}L^{26}$, more preferably one of $L^5$, $L^8$, $L^{11}$, $L^{12}$, $L^{16}$, $L^{17}$, $L^{19}$, $L^{21}$ and $L^{26}$.

In one embodiment, linker L is $L^1$ and $R^1$ and $R^2$ are joined together in a cyclic structure via a second linker $L^1$, thus forming a six-membered piperazine ring including in total four carbon atoms from the two linkers, the amide nitrogen atom and the distal nitrogen atom. In one embodiment, linker L is $L^{19}$ and $R^2$ and $R^{2'}$ are joined together in a cyclic structure via a second linker $L^3$, thus forming a six-membered piperidene ring including in total five carbon atoms from the linkers and the distal nitrogen atom.

In a preferred embodiment, the compound is represented by general structure (I), wherein:
- L is a linker between the amide nitrogen atom and the distal nitrogen atom;
- N* is according to structure (IIa);
- T is according to structure (IIIa) or (IIIb), wherein $R^7$ is a $C_1$-$C_6$ alkyl moiety;
- $R^1$ is selected from hydrogen (H), $C_1$-$C_6$ alkyl or $C_1$-$C_6$ alkenyl, or $R^1$ is joined with a backbone atom of the linker L in a cyclic structure;
- $R^2$ is joined with a backbone atom of the linker L to form a cyclic structure selected from a piperidine ring, a pyrrolidine ring, an imidazolidine ring, a pyrazolidine ring or an azepane ring; and
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety.

In an alternative preferred embodiment, the compound according to the invention is represented by general structure (I), wherein
- L is a linker between the amide nitrogen atom and the distal nitrogen atom comprising 3-10 backbone atoms, or 2 backbone atoms of which one is connected to the distal nitrogen atom via a second linker;
- N* is according to structure (IIIb);
- T is according to structure (IIIa) or (IIIb), wherein $R^7$ is a $C_1$-$C_6$ alkyl moiety;
- $R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
- $R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety;
- $R^4$ is selected from hydrogen (H) or $C_1$-$C_6$ alkyl, wherein the alkyl moiety may be substituted with one or more halogen atoms or (halo)alkoxy moieties; and
- X is an anion, preferably a pharmaceutically acceptable anion.

Particularly preferred compounds in the context of the present invention are identified here below by structures (VI)-(IX). Thus, in a preferred embodiment, the compound of general structure (I) is represented by structure (VI):

(VI)

Herein, $R^2$ is joined with a backbone atom via a second linker forming a cyclic structure, thus N* is $-NR^3$ or $-N^+R^3R^4X^-$. Herein, $R^3$, $R^4$, X and T are as defined above. Preferably, T is according to structure (IIIa) or (IIIb), more preferably according to structure (IVa) or (IVb), most preferably according to structure (IIIa) or (IVa). In the compound according to structure (VI), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VI) may be (R,R); (S,R); (R,S); or (S,S), preferably it is (S,R).

In a preferred embodiment, the compound of general structure (I) is represented by structure (VIIa) or (VIIb):

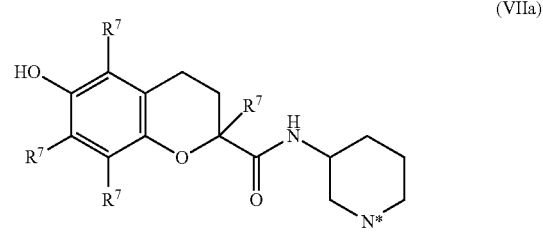

(VIIa)

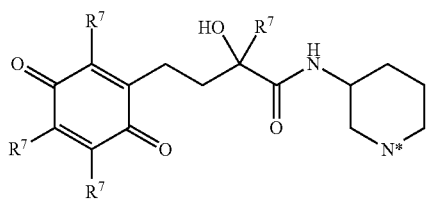

Herein, $R^2$ is joined with a backbone atom via a second linker forming a cyclic structure, thus N* is $—NR^3$ or $—N^+R^3R^4X^-$. Herein, $R^3$, $R^4$, X and $R^7$ are as defined above. In the compound according to structure (VIIa) or (VIIb), $R^7$ is preferably methyl. In the compound according to structure (VIIa) or (VIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIa) or (VIIb) may be (R,R); (S,R); (R,S); or (S,S), preferably it is (S,R). In one embodiment, the compound of general structure (I) is represented by structure (VIIa). In an alternative embodiment, the compound of general structure (I) is represented by structure (VIIb). In highly preferred embodiments, the invention provides a compound for use as described above, wherein the compound is represented by structure (VIIa), wherein each $R^7$ is methyl; N* is $—NR^3$ or $N^+R^3R^4X^-$; X is as defined above and is preferably $Cl^-$; $R^3$ is as defined above and is preferably hydrogen; and $R^4$ is as defined above and is preferably hydrogen. It is even more preferred for this compound to be of the S,R configuration.

In a preferred embodiment, the compound of general structure (I) is represented by structure (VIIIa) or (VIIIb):

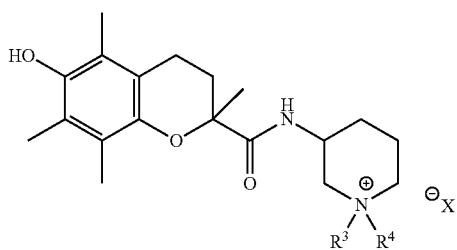

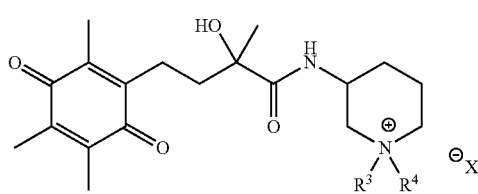

Herein, $R^2$ is joined with a backbone atom via a second linker forming a cyclic structure and N* is $—N^+R^3R^4X^-$. Herein, $R^3$, $R^4$ and X are as defined above. In the compound according to structure (VIIIa) or (VIIIb), $R^3$ is preferably H or $C_1$-$C_2$ alkyl, most preferably $R^3$ is H. In the compound according to structure (VIIIa) or (VIIIb), $R^4$ is preferably H or $C_1$-$C_2$ alkyl, most preferably $R^4$ is H. In the compound according to structure (VIIIa) or (VIIIb), X is preferably Cl, I, TFA or formate, most preferably X is Cl. In the compound according to structure (VIIIa) or (VIIIb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (VIIIa) or (VIIIb) may be (R,R); (S,R); (R,S); or (S,S), preferably it is (S,R). In one embodiment, the compound of general structure (I) is represented by structure (VIIIa). In an alternative embodiment, the compound of general structure (I) is represented by structure (VIIIb).

In a preferred embodiment, the compound of general structure (I) is represented by structure (IXa) or (IXb):

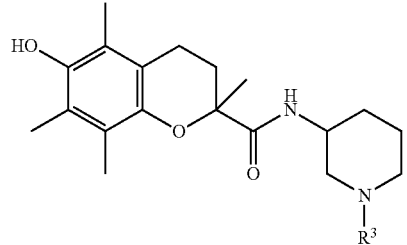

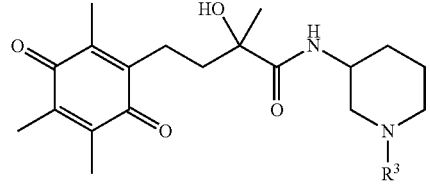

Herein, $R^2$ is joined with a backbone atom via a second linker forming a cyclic structure and N* is $—NR^3$. Herein, $R^3$ is as defined above. In the compound according to structure (VIIIa) or (VIIIb), $R^3$ is preferably H or $C_1$-$C_2$ alkyl, most preferably $R^3$ is H. In the compound according to structure (IXa) or (IXb), the carbon atom at the 2-position of T may be in R-configuration or in S-configuration, preferably it is in S-configuration. Likewise, the carbon atom at the 2-position of the piperidine ring may be in R-configuration or in S-configuration, preferably it is in R-configuration. Thus, the configuration of the compounds according to structure (IXa) or (IXb) may be (R,R); (S,R); (R,S); or (S,S), preferably it is (S,R). In one embodiment, the compound of general structure (I) is represented by structure (IXa). In an alternative embodiment, the compound of general structure (I) is represented by structure (IXb).

In a preferred embodiment, the compound is according to general structure (I), wherein T is represented by structure (IVa) or (IVb), N* is represented by structure (IIa) or by structure (IIb) wherein $R^4$=H and X=Cl, and wherein:
(A) L=$L^1$, $R^1$-$R^2$=$L^1$, $R^3$=H;
(B) L=$L^1$, $R^1$=H, $R^2$=H, $R^3$=H;
(C) L=$L^2$, $R^1$=H, $R^2$=H, $R^3$=H;
(D) L=$L^3$, $R^1$=H, $R^2$=H, $R^3$=H;
(E) L=$L^4$, $R^1$=H, $R^2$=H, $R^3$=absent;
(F) L=$L^5$, $R^1$=H, $R^2$=H, $R^3$=absent;
(G) L=$L^6$, $R^1$=H, $R^2$=H, $R^3$=absent;
(H) L=$L^3$, $R^1$=H, $R^2$=Me, $R^3$=Me;
(I) L=$L^1$, $R^1$=H, $R^2$=Me, $R^3$=Me;
(J) L=$L^7$, $R^1$=H, $R^2$=H, $R^3$=absent;

(K) L=L$^8$, R$^1$=H, R$^2$=H, R$^3$=absent;
(L) L=L$^9$, R$^1$=H, R$^2$=H, R$^3$=absent;
(M) L=L$^{10}$, R$^1$-R$^{1'}$=L$^1$, R$^2$=H, R$^3$=absent;
(N) L=L$^{11}$, R$^1$=H, R$^2$=H, R$^3$=H;
(O) L=L$^{12}$, R$^1$=H, R$^2$=H, R$^3$=absent;
(P) L=L$^{13}$, R$^1$=H, R$^2$=H, R$^3$=H;
(Q) L=L$^{14}$, R$^1$=H, R$^2$=H, R$^3$=H;
(R) L=L$^{15}$, R$^1$=H, R$^2$=H, R$^3$=H;
(S) L=L$^{11}$, R$^1$=H, R$^2$=Me, R$^3$=Me;
(T) L=L$^{16}$, R$^1$=H, R$^2$=H, R$^3$=H;
(U) L=L$^{17}$, R$^1$=H, R$^2$=H, R$^3$=H;
(V) L=L$^{16}$, R$^1$=H, R$^2$=Me, R$^3$=Me;
(W) L=L$^{18}$, R$^1$=H, R$^2$-R$^{2'}$=L$^3$, R$^3$=H;
(X) L=L$^{19}$, R$^1$=H, R$^2$-R$^{2'}$=L$^3$, R$^3$=H;
(Y) L=L$^{20}$, R$^1$=H, R$^2$=H, R$^5$-R$^{5'}$=L$^3$, R$^3$=absent;
(Z) L=L$^{21}$, R$^1$=H, R$^2$-R$^{2'}$=L$^1$, R$^3$=H;
(AA) L=L$^{22}$, R$^1$-R$^{1'}$=L$^1$, R$^2$=H, R$^3$=H;
(AB) L=L$^{23}$, R$^1$-R$^{1'}$=L$^1$, R$^2$=H, R$^3$=H;
(AC) L=L$^{24}$, R$^1$-R$^{1'}$=L$^3$, R$^2$=H, R$^3$=H;
(AD) L=L$^{25}$, R$^1$-R$^{1'}$=L$^3$, R$^2$=H, R$^3$=absent;
(AE) L=L$^{26}$, R$^1$=H, R$^2$=H, R$^5$-R$^{5'}$=L$^1$, R$^3$=H.
(AF) L=L$^{19}$, R$^1$=H, R$^2$-R$^{2'}$=L$^3$, R$^3$=Me;
(AG) L=L$^{19}$, R$^1$=H, R$^2$-R$^{2'}$=L$^1$, R$^3$=H;
(AH) L=L$^{21}$, R$^1$=H, R$^2$-R$^{2'}$=L$^1$, R$^3$=Me;
(AI) L=L$^{27}$, R$^1$=H, R$^2$-R$^{2'}$=—CH$_2$—, R$^3$-R$^{3'}$=L$^1$, R$_4$=H, X=Cl;
(AJ) L=L$^{28}$, R$^1$=H, R$^2$=H, R$^3$=H, R$^4$=H, X=Cl.

It is thus preferred that the compound according to structure (I) is selected from compounds A-AJ defined above, more preferably from compounds A-AH defined above, even more preferably selected from compounds A-AJ based on general structure (IVb), most preferably selected from compounds A-AH based on general structure (IVb). Especially preferred compounds are selected from F, K, N, O, U, V, T, X, Z, AE, AF, AG, AH, AI, and AJ, more preferred compounds are selected from F, K, N, O, U, V, T, X, Z, AE, AF, AG and AH, even more preferably N, T, X and AE, most preferably X. Herein, N* is preferably represented by structure (IIb) wherein R$^4$=H and X=Cl, and the compound is preferably of general structure (IVb).

Compound F may have the R-configuration, the S-configuration or a mixture thereof, preferably compound F is a mixture of the R- and S-enantiomers, more preferably a racemic mixture. Compound K may have the R-configuration, the S-configuration or a mixture thereof, preferably compound K is a mixture of the R- and S-enantiomers, more preferably a racemic mixture. Compound N may have the R,R-configuration, R,S-configuration, S,R-configuration, the S,S-configuration or any mixture thereof, preferably compound N has the R,R-configuration or the S,R-configuration, most preferably the R,R-configuration. Compound O may have the R,R-configuration, R,S-configuration, S,R-configuration, the S,S-configuration or any mixture thereof, preferably compound O is a mixture of the R,S- and S,S-diastereomers more preferably about 1/1 (mol/mol) mixture. Compound U may have the R-configuration, the S-configuration or a mixture thereof, preferably compound U has the R-configuration or the S-configuration. Compound V may have the R-configuration, the S-configuration or a mixture thereof, preferably compound V has the R-configuration. Compound T may have the R-configuration, the S-configuration or a mixture thereof, preferably compound T has the R-configuration or the S-configuration, most preferably the R-configuration. Compound X may have the R,R-configuration, R,S-configuration, S,R-configuration, the S,S-configuration or any mixture thereof, preferably compound X has the R,S-configuration or the S,R-configuration, most preferably the S,R-configuration. Compound Z may have the R-configuration, the S-configuration or a mixture thereof, preferably compound Z is a mixture of the R- and S-enantiomers, more preferably a racemic mixture. Compound AE may have the R,trans-configuration, R,cis-configuration, S,trans-configuration, the S,cis-configuration or any mixture thereof, preferably compound AE has the R,trans-configuration or the S,trans-configuration, most preferably the R,trans-configuration. Compound AF may have the R,R-configuration, R,S-configuration, S,R-configuration, the S,S-configuration or any mixture thereof, preferably compound AF has the S,R-configuration. Compound AG may have the R,R-configuration, R,S-configuration, S,R-configuration, the S,S-configuration or any mixture thereof, preferably compound AG has the S,S-configuration or the S,R-configuration. Compound AH may have the R-configuration, the S-configuration or a mixture thereof, preferably compound AH has the S-configuration. Herein, the first designator (R or S) of the configuration is for the 2-position of T, and in case an additional stereocenter is present in the compound according to the invention, the second designator thereof defines the configuration thereof. Compound AJ may have the R,R-configuration, the R,S-configuration, the S,R-configuration, the S,S-configuration, or a mixture thereof, preferably compound AJ has the S,R-configuration or the R,R-configuration or a mixture thereof, most preferably compound AJ has the R,R-confuguration.

Highly preferred compounds include compound N in the R,R-configuration (R,R-N), compound T in the R-configuration (R-T), compound AE in the R,trans-configuration (R,trans-AE), compound AJ in the R-configuration (R-AJ), and compound X in any configuration. The most preferred compounds include compound N in the R,R-configuration (R,R-N), compound T in the R-configuration (R-T), compound AE in the R,trans-configuration (R,trans-AE) and compound X in any configuration, most preferably the compound according to the invention is compound X in the S,R-configuration (S,R-X). In one embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein N* is represented by structure (IIb), wherein R$^4$=H and X=Cl, more preferably the compound according to the invention is compound X in the S,R-configuration (S,R-X), wherein N* is represented by structure (IIb), wherein R$^4$=H and X=Cl. In one embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein N* is represented by structure (IIa), most preferably the compound according to the invention is compound X in the S,R-configuration (S,R-X), wherein N* is represented by structure (IIa).

In one embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIb), most preferably the compound according to the invention is compound X in the S,R-configuration (S,R-X), wherein the compound is of structure (IIIb).

In one embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIb), wherein N* is represented by structure (IIb), wherein $R^4$=H and X=Cl, most preferably the compound according to the invention is compound X in the S,R-configuration (S,R-X), wherein the compound is of structure (IIb) and wherein N* is represented by structure (IIb), wherein $R^4$=H and X=Cl.

In another embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIb), wherein N* is represented by structure (IIa), most preferably the compound according to the invention is compound X in the S,R-configuration (S,R-X), wherein the compound is of structure (IIIb) and wherein N* is represented by structure (IIa).

In one preferred embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIa), most preferably the compound according to the invention is compound X in the S,R-configuration (S,R-X), wherein the compound is of structure (IIIa).

In one highly preferred embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIa), wherein N* is represented by structure (IIb), wherein $R^4$=H and X=Cl, most preferably the compound according to the invention is compound X in the S,R-configuration (S,R-X), wherein the compound is of structure (IIIa) and wherein N* is represented by structure (IIb), wherein $R^4$=H and X=Cl.

In another highly preferred embodiment, these most preferred compounds according to the invention are compound N in the R,R-configuration (R,R-N), compound T in the R-configuration (R-T), compound AE in the R,trans-configuration (R,trans-AE) and compound X in any configuration, and optionally compound AJ preferably as R,R-AJ, wherein the compound is of structure (IIIa), wherein N* is represented by structure (IIa), most preferably the compound according to the invention is compound X in the S,R-configuration (S,R-X), wherein the compound is of structure (IIIa) and wherein N* is represented by structure (IIa).

The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

Compounds for use according to the invention can be prepared as described in WO2014/011047 and in WO2017/060432.

According to this invention, compounds as described above are for use in treating, preventing or suppressing symptoms associated with at least one of:
a) a mood disorder; and,
b) headache and/or migraine.

Accordingly, compounds as described above are for use in treating, preventing, or suppressing symptoms associated with at least one of a mood disorder, headache, and migraine.

As stated above, in a first aspect, the invention therefore concerns a method of treating, preventing or suppressing symptoms associated with a mood disorder, the method comprising administering to a subject in need thereof, an effective amount of one or more compounds of the invention as defined herein below. In a preferred embodiment of this aspect, the mood disorder comprises depression.

Mood disorders, such as depression, may be diagnosed when a subject exhibits certain symptoms of such disorders. Symptoms of a mood disorder may include: apathy, persistent feelings of sadness, feeling hopeless or helpless, having low self-esteem, feeling inadequate, excessive guilt, feelings of wanting to die, loss of interest in usual activities or activities once enjoyed, difficulty with relationships, sleep disturbances, changes in appetite or weight, decreased energy, difficulty concentrating, a decrease in the ability to make decisions, suicidal thoughts or attempts, frequent physical complaints (e.g., headache, stomach ache and fatigue), running away or threats of running away from home, hypersensitivity to failure or rejection, irritability, hostility, and aggression.

Accordingly, treatment of a mood disorder according to the present invention may include eliminating or reducing the frequency or severity of any of the noted symptoms or other symptoms relied upon by a subject or a medical professional in making a diagnosis of a mood disorder. Thus, in some embodiments, the present invention includes treating a subject exhibiting at least one symptom of a mood disorder by administering to the subject a compound of the invention as herein defined above, alone, or in combination with one or more additional active agents as described herein, in an amount effective to eliminate or reduce the frequency or severity of the symptom. In particular embodiments, the mood disorder is depression. In other embodiments, the invention may specifically be described as eliminating or reducing the frequency or severity of any one of the specific symptoms of a mood disorder as provided above.

In a specific embodiment, the method includes eliminating or reducing the frequency or severity of a specific symptom of depression. In such embodiments, the method can include administering to a subject a compound of the invention as herein defined above, alone, or in combination with one or more additional active agents as described herein. Effectiveness of the method may be established through analysis of a treated subject, through self-reporting of the treated subject or through a diagnosis of effective treatment provided by a medical professional after evaluating the treated subject. In a preferred embodiment, the effectiveness of the method is determined using the Beck Depression Index (BDI) and/or the Hospital Anxiety and Depression Scale (HADS), wherein the BDI is preferably the BDI-II (Beck et al., 1996, J Personality Assessment. 67: 588-97).

In another embodiment, treatment of a mood disorder according to the present invention can further comprise the administration or use one or more additional active agents for treating a mood disorder. Such additional active agents can be but need not be administered simultaneously with the administration of the compound of the invention. Preferably, the additional active agent is selected from a norepinephrine reuptake inhibitor, a selective serotonin reuptake inhibitor, a tricyclic antidepressant, a monoamine oxidase inhibitor, and combinations thereof.

Norepinephrine reuptake inhibitors are also known or noradrenaline reuptake inhibitors, and generally function to elevate the level of norepinephrine in the central nervous system by inhibiting reuptake of norepinephrine from the synaptic cleft into the presynaptic neuronal terminal. Norepinephrine is a catecholamine and phenylethylamine that functions as a neurotransmitter and is known to affect many conditions. The term "norepinephrine reuptake inhibitor" includes any compound typically recognized as inhibiting the reuptake of norepinephrine in the central nervous system. Non-limiting examples of norepinephrine reuptake inhibitors useful according to the invention include atomoxetine, reboxetine, viloxazine, maprotiline, bupropion, radafaxine, and combinations thereof.

Non-limiting examples of specific selective serotonin reuptake inhibitors useful according to the invention include fluoxetine, paroxetine, citalopram, escitalopram, fluvoxamine, sertraline, and combinations thereof.

Tricyclic antidepressants are a class of antidepressant compounds that can be described as including any compound exhibiting antidepressant activity and having a chemical formula including a fused three ring structure. Exemplary tricyclic antidepressants for use according to the present invention include, but are not limited to, amitriptyline, amoxapine, butriptyline, clomipramine, desipramine, dibenzepin, dosulepin, doxepin, imipramine, lofepramine, nortriptyline, protriptyline, trimipramine, and combinations thereof.

Monoamine oxidase inhibitors include a class of compounds understood to act by inhibiting the activity of monoamine oxidase, an enzyme generally found in the brain and liver, which functions to break down monoamine compounds, typically through deamination. There are two isoforms of monoamine oxidase inhibiting compounds, MAO-A and MAO-B. The MAO-A isoform preferentially deaminates monoamines typically occurring as neurotransmitters (e.g., serotonin, melatonin, epinephrine, norepinephrine, and dopamine). Thus, monoamine oxidase inhibitors have been historically prescribed as antidepressants and for treatment of other social disorders, such as agoraphobia and social anxiety. The MAO-B isoform preferentially deaminates phenylethylamine and trace amines. Dopamine is equally deaminated by both isoforms. Monoamine oxidase inhibitors may by reversible or non-reversible and may be selective for a specific isoform. For example, the monoamine oxidase inhibitor moclobemide (also known as Manerix or Aurorix) is known to be approximately three times more selective for MAO-A than MAO-B. Any compound generally recognized as being a monoamine oxidase inhibitor may be useful according to the present invention. Non-limiting examples of monoamine oxidase inhibitors useful in combination with the compounds of the invention include the following: isocarboxazid, moclobemide, phenelzine, tranylcypromine, selegiline, nialamide, iproniazid, iproclozide, toloxatone, harmala, brofaromine, benmoxin, 5-methoxy-N,N-dimethyltryptamine, 5-methoxy-α-methyltryptamine, and combinations thereof.

As stated above, in a second aspect, the invention therefore concerns a method of treating, preventing or suppressing symptoms associated with at least one of a headache and migraine, the method comprising administering to a subject in need thereof, an effective amount of one or more compounds of the invention as defined herein below.

A headache is a pain in the head, such as in the scalp, face, forehead or neck. A headache can be a primary headache or a secondary headache. A primary headache is a headache which is not caused by another condition. Contrarily, a secondary headache is due to a disease or medical condition, such as an illness, infection, injury, stroke or other abnormality. Thus, with a secondary headache there is an underlying disorder that produces the headache as a symptom of that underlying disorder.

Tension headache is the most common type of primary headache and tension headaches account for about 90% of all headaches. A tension headache is often experienced in the forehead, in the back of the head and neck, or in both regions. It has been described as a tight feeling, as if the head were in a vise. Soreness in the shoulders or neck is common. Nausea is uncommon with a tension headache. In one embodiment, the invention thus pertains to a method of treating, preventing or suppressing symptoms associated with a headache, wherein the headache comprises tension-type headaches.

In a further embodiment, the treatment of a headache according to the present invention can further comprise the administration or use one or more additional active agents for treating a headache. Such additional active agents can be but need not be administered simultaneously with the administration of the compound of the invention. The additional active agent in the treatment is analgesic, e.g. a non-steroidal anti-inflammatory drugs (NSAIDS), including e.g. including diclofenac and ibuprofen, or paracetamol and aspirin and combinations thereof, e.g. with caffeine.

Migraine headaches are recurrent headaches that may be unilateral or bilateral. Migraine headaches may occur with or without a prodrome. The aura of a migraine may consist of neurologic symptoms, such as dizziness, tinnitus, scotomas, photophobia, or visual scintillations (e.g. bright zigzag lines). Migraines without aura are the most common, accounting for more than 80% of all migraines. An estimated 10-20% of the population suffers from migraine headaches. A migraine thus typically includes a unilateral, throbbing moderate to severe headache. Other symptoms of or associated with migraines include, but are not limited to, aura, blurred vision, nausea, vomiting, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, cold and moist feeling in appendages, and sensitivity to light, sound, or smell.

In one embodiment, the invention thus pertains to a method of treating, preventing or suppressing symptoms associated with a migraine, wherein the migraine comprises common migraine, classic migraine, familial hemiplegic migraine, sporadic hemiplegic migraine, migraine with brainstem aura, retinal migraine, recurrent migraine and chronic migraine. A patient is understood to be a chronic or recurrent migraine patient when the patient experiences headaches more than half the time, for 15 days or more in a month, for at least three months.

In a preferred embodiment, the treatment according to the invention eliminates, reduces the severity of and/or reduces the frequency of occurrence of at least one symptom of (or associated with) migraine, whereby preferably the symptoms of (or associated with) migraine are as defined above.

In a further embodiment, the treatment of a migraine according to the present invention can further comprise the administration or use one or more additional active agents for treating a migraine. Such additional active agents can be but need not be administered simultaneously with the administration of the compound of the invention. The additional active agent in the treatment can be a preventive migraine medication such e.g. topiramate, divalproex/sodium valproate, propranolol, or metoprolol. Furthermore, the additional active agent can be an analgesic, a triptan or an ergotamine. Preferred analgesics are NSAIDS, including e.g. including diclofenac and ibuprofen, or paracetamol and aspirin and combinations thereof, e.g. with caffeine. A preferred triptan is e.g. sumatriptan (e.g. in combination with naproxen). Ergotamine and dihydroergotamine are examples of suitable ergotamines.

An "effective amount" of a compound is an amount of a compound which, when administered to a subject, is sufficient to reduce or eliminate either one or more symptoms of a disease, or to retard the progression of one or more symptoms of a disease, or to reduce the severity of one or more symptoms of a disease, or to suppress the manifestation of a disease, or to suppress the manifestation of adverse symptoms of a disease. An effective amount can be given in one or more administrations.

The "effective amount" of that may be combined with the carrier materials to produce a single dosage form will vary depending upon the host to which the active ingredient is administered and the particular mode of administration. The unit dosage chosen is usually fabricated and administered to provide a desired final concentration of the compound in the blood.

The effective amount (i.e. the effective total daily dose), preferably for adults, is herein defined as a total daily dose of about 5 to 2000 mg, or about 10 to 1000 mg, or about 20 to 800 mg, or about 30 to 800 mg or about 30 to 700 mg, or about 20 to 700 mg or about 20 to 600 mg, or about 30 to 600 mg, or about 30 to 500 mg, about 30 to 450 mg or about 30 to 400 mg, or about 30 to 350 mg or about 30 to 300 mg or about 50 to 600 mg, or about 50 to 500 mg, or about 50 to 450 mg, or about 50 to 400 mg or about 50 to 300 mg, or about 50 to 250 mg, or about 100 to 250 mg or about 150 to 250 mg. In the most preferred embodiment, the effective amount is about 200 mg.

Alternatively, the effective amount of the compound, preferably for adults, preferably is administered per kg body weight. The total daily dose, preferably for adults, is therefore about 0.05 to about 40 mg/kg, about 0.1 to about 20 mg/kg, about 0.2 mg/kg to about 15 mg/kg, or about 0.3 mg/kg to about 15 mg/kg or about 0.4 mg/kg to about 15 mg/kg or about 0.5 mg/kg to about 14 mg/kg or about 0.3 mg/kg to about 14 mg/kg or about 0.3 mg/kg to about 13 mg/kg or about 0.5 mg/kg to about 13 mg/kg or about 0.5 mg/kg to about 11 mg/kg.

The total daily dose for children is preferably at most 200 mg. More preferably the total daily dose is about 5 to 200 mg, about 10 to 200 mg, about 20 to 200 mg about 30 to 200 mg about 40 to 200 mg, or about 50 to 200 mg. Preferably, the total daily dose for children is about 5 to 150 mg, about 10 to 150 mg, about 20 to 150 mg about 30 to 150 mg about 40 to 150 mg, or about 50 to 150 mg. More preferably, the total daily dose is about 5 to 100 mg, about 10 to 100 mg, about 20 to 100 mg about 30 to 100 mg about 40 to 100 mg, or about 50 to 100 mg. Even more preferably, the total daily dose is about 5 to 75 mg, about 10 to 75 mg, about 20 to 75 mg about 30 to 75 mg about 40 to 75 mg, or about 50 to 75 mg.

Alternative examples of dosages which can be used are an effective amount of the compounds of the invention within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight.

Compounds of the present invention may be administered in a single daily dose, or the total daily dosage may be administered in divided dosage of two, three or four times daily.

In a preferred embodiment of the invention, "subject", "individual", or "patient" is understood to be an individual organism, preferably a vertebrate, more preferably a mammal, even more preferably a primate and most preferably a human.

The dose as defined herein is preferably suitable for administration to humans. Hence, in a preferred embodiment, the invention pertains to a compound as defined herein above, for use in treating, preventing, or suppressing symptoms associated with mood disorders, headaches and migraine by administration of an effective dose as defined herein, wherein the subject to be treated is a primate, wherein preferably the subject is a human.

In a further preferred embodiment of the invention, the human is an adult, e.g. a person that is 18 years or older. In addition, it is herein understood that the average weight of an adult person is 62 kg, although the average weight is known to vary between countries. In another embodiment of the invention the average weight of an adult person is therefore between about 50-90 kg. It is herein understood that the effective dose as defined herein is not confined to subjects having an average weight. Preferably, the subject has a BMI (Body Mass Index) between 18.0 to 40.0 kg/m$^2$, and more preferably a BMI between 18.0 to 30.0 kg/m$^2$.

Alternatively, the subject to be treated is a child, e.g. a person that is 17 years or younger. In addition, the subject to be treated may be a person between birth and puberty or between puberty and adulthood. It is herein understood that puberty starts for females at the age of 10-11 years and for males at the age of 11-12 year. Furthermore, the subject to be treated may be a neonate (first 28 days after birth), an infant (0-1 year), a toddler (1-3 years), a preschooler (3-5 years); a school-aged child (5-12 years) or an adolescent (13-18 years).

In one embodiment, the invention relates to a compound as defined herein above, for use in treating, preventing, or suppressing symptoms associated with mood disorders, headaches and migraine by administration of an effective dose as defined herein, to a (human) subject suffering from a mitochondrial disorder as herein defined below, whereas in another embodiment the subject to be treated is not a (human) subject suffering from such a mitochondrial disorder. More specifically, the subject to be treated is or is not a (human) subject suffering from a m.3243A>G related mitochondrial disease.

A mitochondrial disorder preferably, but not exclusively, is herein understood to be a mitochondrial disorder with affected oxidative phosphorylation function. A preferred mitochondrial disorder with affected oxidative phosphorylation function is a disorder selected from the group consisting of: Myoclonic epilepsy; Myoclonic Epilepsy with Ragged Red Fibers (MERRF); Leber's Hereditary Optic Neuropathy (LHON); neuropathy, ataxia and retinitis pigmentosa (NARP); Mitochondrial Myopathy, Encephalopathy, Lactic acidosis, Stroke-like episodes (MELAS); Leigh syndrome; Leigh-like syndrome; Dominant Optic atrophy (DOA); Kearns-Sayre Syndrome (KSS); Maternally Inherited Diabetes and Deafness (MIDD); Alpers-Huttenlocher syndrome; Ataxia Neuropathy spectrum; Chronic Progressive External Ophthalmoplegia (CPEO); Pearson syndrome; Mitochondrial Neuro-Gastro-Intestinal Encephalopathy (MNGIE); Sengers syndrome; 3-methylglutaconic aciduria, sensorineural deafness, encephalopathy and neuro-radiological findings of Leigh-like syndrome (MEGDEL); SURF1 Leigh syndrome; myopathy; mitochondrial myopathy; cardiomyopathy; and encephalomyopathy and isolated or combined oxidative phosphorylation disorders.

Mitochondrial diseases may be associated with specific mutations in nuclear DNA (nDNA) and/or mitochondrial DNA (mDNA). In a preferred embodiment of the invention, the mitochondrial disorder or disease or condition associated with mitochondrial dysfunction is therefore associated with one or several specific mutations in nuclear DNA and/or mitochondrial DNA. Non-limiting examples of such causative genes are MT-ND1 (mtDNA gene), NDUFS1 (nDNA gene), POLG (nDNA gene), MT-TL1 (mtDNA gene) and C10ORF2 (nDNA gene) (Niyazov et al, Mol. Syndromol (2016) 7(3):122-137). In a further preferred embodiment of the invention, the mitochondrial disorder is associated with a mutation in the MT-TL1 (mitochondrial encoded tRNA leucine 1) gene. More preferably, the mutation in the MT-TL1 gene is at least one of m.3243A>G, m.3271T>C and m.3251A>G. In a most preferred embodiment, the mitochondrial disorder is associated with a m.3243A>G mutation of the mitochondrial tRNA(Leu) gene.

A compound for use as defined herein (i.e. for use in treating, preventing, or suppressing symptoms associated with mood disorders, headaches and migraine by administration of an effective total daily dose) may be administered as a composition.

The compositions comprising the compounds as described above can be prepared as a medicinal or cosmetic preparation or in various other media, such as foods for humans or animals, including medical foods and dietary supplements. A "medical food" is a product that is intended for the specific dietary management of a disease or condition for which distinctive nutritional requirements exist. By way of example, but not limitation, medical foods may include vitamin and mineral formulations fed through a feeding tube (referred to as enteral administration). A "dietary supplement" shall mean a product that is intended to supplement the human diet and is typically provided in the form of a pill, capsule, and tablet or like formulation. By way of example, but not limitation, a dietary supplement may include one or more of the following ingredients: vitamins, minerals, herbs, botanicals; amino acids, dietary substances intended to supplement the diet by increasing total dietary intake, and concentrates, metabolites, constituents, extracts or combinations of any of the foregoing. Dietary supplements may also be incorporated into food, including, but not limited to, food bars, beverages, powders, cereals, cooked foods, food additives and candies; or other functional foods designed to promote cerebral health or to prevent or halt the progression of a mood disorder, headache and migraine.

The subject compositions thus may be compounded with other physiologically acceptable materials which can be ingested including, but not limited to, foods. In addition or alternatively, the compositions for use as described herein may be administered orally in combination with (the separate) administration of food.

The compositions may be administered alone or in combination with other pharmaceutical or cosmetic agents and can be combined with a physiologically acceptable carrier thereof. In particular, the compounds described herein can be formulated as pharmaceutical or cosmetic compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-P-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003), $21^{st}$ edition (2005) and $22^{nd}$ edition (2012), incorporated herein by reference.

Pharmaceutical or cosmetic compositions containing the compounds for use according to the invention may be in any form suitable for the intended method of administration, including, for example, a solution, a suspension, or an emulsion. In a preferred embodiment, the compound is administered in a solid form or in a liquid form.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water or saline. Such compositions may also comprise adjuvants, such as wetting agents, emulsifying and suspending agents, cyclodextrins, and sweetening, flavoring, and perfuming agents.

Liquid carriers are typically used in preparing solutions, suspensions, and emulsions. In a preferred embodiment, liquid carriers/liquid dosage forms contemplated for use in the practice of the present invention include, for example, water, saline, pharmaceutically acceptable organic solvent(s), pharmaceutically acceptable oils or fats, and the like, as well as mixtures of two or more thereof. In a preferred embodiment, the compound for use as defined herein is admixed with an aqueous solution prior to administration. The aqueous solution should be suitable for administration and such aqueous solutions are well known in the art. It is further known in the art that the suitability of an aqueous solution for administration may be dependent on the route of administration.

In a preferred embodiment, the aqueous solution is an isotonic aqueous solution. The isotonic aqueous solution preferably is almost (or completely) isotonic to blood plasma. In an even more preferred embodiment, the isotonic aqueous solution is saline.

The liquid carrier may contain other suitable pharmaceutically acceptable additives such as solubilizers, emulsifiers, nutrients, buffers, preservatives, suspending agents, thickening agents, viscosity regulators, stabilizers, flavorants and the like. Preferred flavorants are sweeteners, such as monosaccharides and/or disaccharides. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like.

For parenteral administration, the carrier can also be an oily ester such as ethyl oleate, isopropyl myristate, and the like. Compositions for use in the present invention may also be in the form of microparticles, microcapsules, liposomal encapsulates, and the like, as well as combinations of any two or more thereof.

Time-release, sustained release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound as defined herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.Y., p. 33 et seq (1976).

A pharmaceutical or cosmetic composition can comprise a unit dose formulation, where the unit dose is a dose sufficient to have a therapeutic or suppressive effect of a disorder or condition as defined herein. The unit dose may be sufficient as a single dose to have a therapeutic or suppressive effect of a disorder or condition as defined herein. Alternatively, the unit dose may be a dose administered periodically in a course of treatment or suppression of a disorder or condition as defined herein. During the course of the treatment, the concentration of the subject compositions may be monitored to insure that the desired level of the compound of the invention is maintained.

In a preferred embodiment the invention pertains to a compound as defined herein for use in treating, preventing, or suppressing symptoms mediated by or associated with mood disorders, headaches and migraine by administration of an effective total daily dose, and wherein preferably the compound reaches a blood steady state level within 5 days. More preferably steady state levels are reached within 4 days, even more preferably within 3 days and most preferably steady state levels are reached within 2 days after the first administration.

Steady state is herein understood that the overall intake of a compound as defined above is (roughly) in dynamic equilibrium with its elimination. During steady state, the plasma levels of the compound preferably maintained within the effective therapeutic range. Put differently, the levels of the compound in the blood are maintained between the minimum therapeutically effective concentration and the maximum therapeutically effective concentration. Below the minimum concentration, the compound does not have sufficient therapeutic effect to be considered efficacious. Above the maximum concentration, side effects increase eventually leading to toxicity.

To maintain an effective therapeutic range during treatment, the average plasma concentrations ($C_{av}$) of the compound as defined herein is maintained between about 10 ng/ml to about 20000 ng/ml, or about 20 ng/ml to about 10000 ng/ml, or about 30 ng/ml to about 5000 ng/ml, or between about 30 ng/ml to about 4000 ng/ml, or between about 30 ng/ml to about 3000 ng/ml, or between about 30 ng/ml to about 2000 ng/ml, or about 30 ng/ml to about 1000 ng/ml, or between about 50 ng/ml to about 5000 ng/ml, or between about 100 ng/ml to about 5000 ng/ml, or between about 50 ng/ml to about 4000 ng/ml, or between about 50 ng/ml to about 3000 ng/ml, or between about 50 ng/ml to about 2000 ng/ml, or between about 50 ng/ml to about 1000 ng/ml. In a more preferred embodiment, the average plasma concentration of the compound is maintained between about 50 ng/ml-500 ng/ml or 100 ng/ml-500 ng/ml.

The average plasma concentrations may be determined using any conventional method known in the art. However in a preferred embodiment, the plasma concentrations are determined by extracting the compound as defined herein from human plasma by protein precipitation, followed by Liquid Chromatography-Tandem Mass Spectrometry (LC-MS/MS). The concentration of the compound may subsequently be determined using calibration standards.

The compound as defined herein may be metabolized and instead of, or in addition to the non-metabolized compound, the effective therapeutic range of the metabolized compound may be maintained during treatment. In a preferred embodiment of the invention, the average plasma concentrations ($C_{av}$) of the metabolized compound is maintained between about 5 ng/ml to about 5000 ng/ml, or about 10 ng/ml to about 2000 ng/ml, or about 20 ng/ml to about 1000 ng/ml, or between about 20 ng/ml to about 800 ng/ml, or between about 20 ng/ml to about 600 ng/ml, or between about 20 ng/ml to about 400 ng/ml, or about 20 ng/ml to about 200 ng/ml, or between about 30 ng/ml to about 1000 ng/ml, or between about 50 ng/ml to about 1000 ng/ml, or between about 30 ng/ml to about 800 ng/ml, or between about 30 ng/ml to about 600 ng/ml, or between about 30 ng/ml to about 400 ng/ml, or between about 30 ng/ml to about 200 ng/ml. In a more preferred embodiment, the average plasma concentration of the compound is maintained between about 40 ng/ml-500 ng/ml or 50 ng/ml-200 ng/ml.

During or after administration of the compound as defined herein, the maximum plasma concentrations ($C_{max}$) remain below about 20000 ng/ml or below 10000 ng/ml or below 5000 ng/ml or below about 4000 ng/ml or below about 3000 ng/ml or below about 2000 ng/ml or below about 1000 ng/ml. In the most preferred embodiment, the maximum plasma concentrations remain below about 500 ng/ml.

Similarly, the maximum plasma concentrations of the metabolized compound remain below about 5000 ng/ml, or 2000 ng/ml, or 1000 ng/ml, or below about 800 ng/ml or below about 600 ng/ml or below about 400 ng/ml. In the most preferred embodiment, the maximum plasma concentrations of the metabolized compound remain below about 250 ng/ml.

To maintain an effective range during treatment, the compound may be administered once a day, or once every two, three, four or five days. However preferably, the compound may be administered at least once a day. Hence in a preferred embodiment, the invention pertains to a compound as defined herein above, for use in treating, preventing, or suppressing symptoms mediated by or associated with mood disorders, headaches and migraine by administration of an effective total daily dose, wherein the effective dose is defined herein above. The total daily dose may be administered as a single daily dose. Alternatively, the compound is administered at least twice daily. Hence, the compound as defined herein may be administered once, twice, three, four or five times a day. As such, the total daily dose may be divided over the several doses (units) resulting in the administration of the total daily dose as defined herein. In a preferred embodiment, the compound is administered twice daily. It is further understood that the terms "twice daily", "bid" and "bis in die" can be used interchangeable herein.

In a preferred embodiment, the total daily dose is divided over several doses per day. These separate doses may differ in amount. For example for each total daily dose, the first dose may have a larger amount of the compound than the second dose or vice versa. However preferably, the compound is administered in similar or equal doses. Therefore in a most preferred embodiment, the compound is administered twice daily in two similar or equal doses.

In a further preferred embodiment of the invention, the total daily dose of the compound as defined herein above is administered in at least two separate doses. The interval between the administration of the at least two separate doses is at least about 0.5, 1, 2, 3, 4, 5, 6, 7, 8, 9, 10, 11 or 12 hours, preferably the interval between the at least two separate doses is at least about 4, 5, 6, 7, 8, 9, 10, 11 or 12 hours and more preferably the interval between the at least two separate doses is at least about 8, 9, 10, 11 or 12 hours.

The composition can be administered in an effective total daily dose as defined herein, either as a prophylaxis or treatment, to a patient in any of a number of methods. In particular, the method of administration can vary based on the individual subject, the condition or the stage of disease, and other factors evident to one skilled in the art.

The compounds for a use as defined herein may be administered enterally, orally, parenterally, sublingually, by inhalation (e. g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e. g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds are mixed with pharmaceutically acceptable carriers, adjuvants, and vehicles appropriate for the desired route of administration. Oral administration is a preferred route of administration, and formulations suitable for oral administration are preferred formulations. Alternatively, the compounds may be administered by supplementation via gastric or percutaneous tubes.

Hence, in a preferred embodiment the invention pertains to a compound as defined herein above, for use in treating, preventing, or suppressing symptoms mediated by or associated with mood disorders, headaches and migraine by administration of an effective total daily dose, wherein compound is administered orally.

The oral route is the preferred means of administration and (at least for adults) preferably the dosage form used is a solid oral dosage form. The class of solid oral dosage forms consists primarily of tablets and capsules, although other forms are known in the art and can be equally suitable. When used as a solid oral dosage form, the compound as defined herein may e.g. be administered in the form of an immediate release tablet (or a capsule and the like) or a sustained release tablet (or a capsule and the like). Any suitable immediate release or sustained release solid dosage forms can be used in the context of the invention as will be evident for the skilled person.

The compounds described for use as described herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

While the compounds for use as described herein can be administered as the sole active pharmaceutical (or cosmetic) agent, they can also be used in combination with one or more other agents used in the treatment or suppression of disorders.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

REFERENCES

Ahmed, F. (2012). Headache disorders: differentiating and managing the common subtypes. Br. J. Pain 6: 124-32.

Ashina, S., et al., (2012). Depression and risk of transformation of episodic to chronic migraine. J. Headache Pain 13: 615-624.

Bansal, Y., and Kuhad, A. (2016). Mitochondrial Dysfunction in Depression. Curr. Neuropharmacol. 14: 610-618.

Fuller-Thomson, E., et al., (2013). Depress. Res. Treat. 2013: 1-10.

Goadsby, P. J., Lipton, R. B., and Ferrari, M. D. (2002). Migraine Current Understanding and Treatment. N. Engl. J. Med. 346: 257-270.

Janssen, M. C. H. et al., 2018, Clin. Pharm. Ther. DOI: 10.1002/cpt.1197

Kalra, A. A., and Elliott, D. (2007). Acute migraine: Current treatment and emerging therapies. Ther. Clin. Risk Manag. 3: 449-59.

Koene, S., et al., (2009). Major depression in adolescent children consecutively diagnosed with mitochondrial disorder. J. Affect. Disord. 114: 327-332.

Kraya, T., et al., (2017). Prevalence of Headache in Patients With Mitochondrial Disease: A Cross-Sectional Study. Headache J. Head Face Pain.

Obermann, M., and Holle, D. (2016). Recent advances in the management of migraine. F1000Research 5: 2726.

Verhaak, C., Laat, P. De, Koene, S., Tibosch, M., Rodenburg, R., Groot, I. De, et al. Quality of life, fatigue and mental health in patients with the m.3243A > G mutation and its correlates with genetic characteristics and disease manifestation.

Vollono, C., Primiano, G., Marca, G. Della, Losurdo, A., and Servidei, S. (2017). Migraine in mitochondrial disorders: Prevalence and characteristics. Cephalalgia 33310241772356.

Yang, Y., et al., (2016). Familial Aggregation of Migraine and Depression: Insights From a Large Australian Twin Sample. Twin Res. Hum. Genet. 19: 312-21.

EXAMPLES

Example 1

Khenerdy Study

The Khenergy trial (clinicaltrial.gov identifier NCT02909400) was a double blind, randomized, placebo-controlled, single-centre, two-way cross-over trial. Twenty patients, with a confirmed mitochondrial DNA tRNALeu (UUR) m.3243A>G mutation and with clinical signs of mitochondrial disease, were randomized over 2 groups (active or placebo first). After a screening period and a training session, each group had 2 dosing periods of 28 days, with a washout period of at least 28 days in between. On these occasions (i.e. during the dosing periods), patients received 100 mg KH176 twice daily (treatment A) or a matching placebo (treatment B) twice daily for 28 days. Clinical assessments were performed once in a training session prior to baseline, at baseline and in week 4 post dosing during each treatment phase (A and B). Testing conditions and circumstances, with respect to timing of the assessments, hospitalization and meals, were standardized for each assessment period. Furthermore, assessments of biomarkers for mitochondrial functioning, pharmacokinetics and specific safety assessments were performed weekly. Trial results have been published (Janssen, Koene, De Laat, et al., 2018)

KH176 Effect on Depression

The effect of KH176 on depression symptoms in patients carrying the mutation m.3243A>G in the mitochondrial DNA was evaluated with the Beck Depression Inventory-II (BDI) score and Hospital Anxiety and Depression Scale (HADS) during the Khenergy phase 2 clinical trial (clinicaltrial.gov identifier NCT02909400). The Beck Depression Inventory showed statistical differences between the KH176 and placebo treatment period on the total score (effect size, −2.9 (95% Cl, −5.7 to −0.13); P=0.04) and the affective subscale (effect size, −1.1 (95% Cl, −1.7 to −0.4); P=0.004). This observation was supported by a positive trend in the Hospital Anxiety and Depression Scale (effect size, −1.9 (95% Cl, −3.6 to −0.2); P=0.03).

TABLE 1

Beck Depression Inventory-II and Hospital Anxiety and Depression Scale. Estimate of the treatment effect and p-values between the treatment (KH176) and Placebo.

| Endpoint | Comparison KH176-Placebo | |
|---|---|---|
| | Effect size | P value |
| Beck Depression Inventory | −2.9 | 0.041 |
| Beck Depression Affective Subscale | −1.1 | 0.004 |
| Hospital Anxiety and Depression Scale | 1.9 | 0.03 |

KH176 Effect on Migraine

Two patients from the Khenergy Phase 2 clinical trial have spontaneously reported a decreased frequency of migraine event during the treatment period with KH176 (reported before unblinding of the study). A third patient retrospectively reported that he had more migraines during the placebo treatment period over the KH176 treatment period. All other patients included in the study did not have migraines revealing that KH176 had a positive effect on migraine in 3 out of 3 patients who suffer from chronic migraine.

Patient Reports from Khenergy Study:

Patient A: "For years I had severe headaches every day and migraine 2 times a week. I used pain and migraine medication each day. Three days after starting KH176 I had no headache anymore, during the 4 weeks that I took it, I had NO headache and took NO medication. Unfortunately 3 days after stopping KH176 the headache and migraine came back as severe as before."

Patient B: "I always have migraine 4 times a week, even during holidays. During the KH176 period I had less headaches and migraine, 0 to 2 times a week. After stopping the medication the migraine returned as never before."

Patient C: "In retrospect this patient reported more migraine in the Placebo arm."

The invention claimed is:

1. A method of treating, preventing or suppressing symptoms associated with at least one of:
   a) a mood disorder, wherein the mood disorder comprises depression, or wherein the symptoms of the mood disorder include at least one of apathy, persistent feelings of sadness, feelings of hopelessness or helplessness, having low self-esteem, feeling inadequate, excessive guilt, feelings of wanting to die, loss of interest in usual activities or activities once enjoyed, difficulty with relationships, sleep disturbances, changes in appetite or weight, decreased energy, difficulty concentrating, a decrease in the ability to make decisions, suicidal thoughts or attempts, frequent physical complaints, running away or of threats of running away front home, hypersensitivity to failure or rejection, irritability, hostility, or aggression; and,
   b) headache and/or migraine, wherein the headache comprises tension-type headaches or wherein the migraine comprises common migraine, classic migraine, familial hemiplegic migraine, sporadic hemiplegic migraine, migraine with brainstem aura, retinal migraine, recurrent migraine and chronic migraine, or wherein the treatment eliminates, reduces the severity of, and/or reduces the frequency of occurrence of at least one symptom of tension-type headaches or migraine, which symptom includes at least one of moderate to severe headaches, and associated symptoms including aura, blurred vision, nausea, vomiting, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, cold and moist feeling in appendages, and sensitivity to light, sound, or smell;

the method comprising administering to a subject in need thereof an effective amount of a compound represented by general structure (I):

(I)

wherein,
T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;

L is a linker between the amide nitrogen atom and the distal nitrogen atom comprising 1 to 10 optionally substituted backbone atoms selected from carbon, nitrogen and oxygen;

N* is represented by structure (IIa) or (IIb)

(IIa)

(IIb)

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with a backbone atom of the linker L in a cyclic structure; and $R^4$ is selected from hydrogen (H) or $C_1$-$C_6$ alkyl, wherein the alkyl moiety may be substituted with one or more halogen atoms or (halo)alkoxy moieties; and X is an anion.

2. The method according to claim 1, wherein the method is for treating, preventing or suppressing symptoms associated with a mood disorder.

3. The method according to claim 1, wherein the method is for treating, preventing or suppressing symptoms associated with headache and/or migraine.

4. The method according to claim 1, wherein the method is for treating or suppressing symptoms associated with at least one of:
a) a mood disorder; and,
b) headache and/or migraine.

5. The method according to claim 1, wherein the compound is represented by structure (VI):

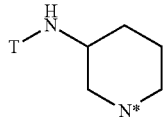

(VI)

wherein, N* is $-NR^3$ or $-N^+R^3R^4X^-$, wherein T, X, $R^3$, and $R^4$ are as defined in claim 1.

6. The method according to claim 1, wherein T is represented by structure (IIIa) or (IIIb):

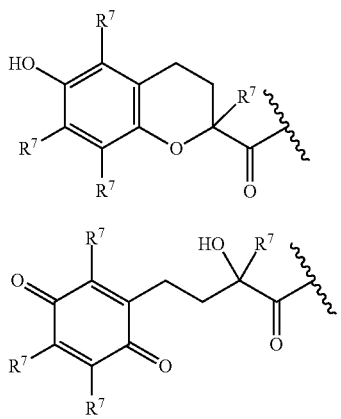

(IIIa)

(IIIb)

wherein $R^7$ is individually a $C_1$-$C_6$ alkyl moiety.

7. The method according to claim 1, wherein the treatment eliminates, reduces the severity of, and/or reduces the frequency of occurrence of at least one symptom of the mood disorder.

8. The method according to claim 1, wherein the treatment further comprises the administration of an additional active agent selected from the group consisting of a preventive migraine medication, an analgesic, a triptan and an ergotamine.

9. The method according to claim 1, wherein the total daily dose that is administered is in the range of about 5 to 2000 mg.

10. The method according to claim 1, wherein the compound is administered orally.

11. The method according to claim 1, wherein the compound is administered at least twice daily.

12. The method according to claim 11, wherein the interval between two administrations is at least about 1, 2, 3, 4, 5, 6, 7, 8, 9, 10, 11 or 12 hours.

13. The method according to claim 1, wherein the linker L is selected from:
$-(CH_2)_2-$,
$-(CH_2)_2NHC(O)CH_2-$,
$-(CH_2)_3-$,
$-(CH_2)_2NHC(NH_2)=$,
$-(CH_2)_2NHC(O)CH_2NHC(NH_2)=$,
$-(CH_2)_3NHC(NH_2)=$,
$-(CH_2)_2NHC(Me)=$,
$-(CH_2)_2NHC(O)CH_2NHC(Me)=$,
$-(CH_2)_3NHC(Me)=$,
$-(CH_2)_2NR^{1'}C(NH_2)=$,
$-C(CO_2H)(CH_2)_3-$,
$-C(CO_2H)(CH_2)_3NHC(NH_2)=$,
$-C(CO_2H)CH_2-$,
$-C(CO_2H)(CH_2)_2-$,
$-C(CO_2H)(CH_2)_4-$,
$-(CH_2)_4-$,
$-(CH_2)_5-$,
$-CHR^{2'}C(O)-$,
$-CHR^{2'}CH_2-$,
$-CHR^5CH_2NR^{5'}C(Me)=$,
$-CHR^{2'}(CH_2)_2-$,
$-(CH_2)_2CHR^{1'}-$,
$-(CH_2)_2CHR^{1'}NHC(O)C(Me)-$,
$-CH_2CHR^{1'}-$,
$-CH_2CHR^{1'}NHC(Me)=$,
$-CHR^5(CH_2)_2CHR^{5'}-$,
$-CHR^{2'}CHR^{3'}(CH_2)_2-$, and
$-CR^5=CH-CH=CR^{5'}-CH_2-$, wherein $R^5$ and $R^{5'}$ represent the connection of a second linker between one backbone atom of the linker, bearing $R^5$, and another backbone atom of the linker, bearing $R^{5'}$, wherein $R^{5'}$ is joined with $R^5$ via the second linker, thus forming a 4-10-membered cyclic structure.

14. The method according to claim 1, wherein T is represented by structure (IVa) or (IVb), N* is represented by structure (IIa), or by structure (IIb) wherein $R^4$=H and X=Cl, and wherein:
(A) L=$-(CH_2)_2-$, $R^1$-$R^2$=$-(CH_2)_2-$, $R^3$=H;
(B) L=$-(CH_2)_2-$, $R^1$=H, $R^2$=H, $R^3$=H;
(C) L=$-(CH_2)_2NHC(O)CH_2-$, $R^1$=H, $R^2$=H, $R^3$=H;
(D) L=$-(CH_2)_3-$, $R^1$=H, $R^2$=H, $R^3$=H;
(E) L=$-(CH_2)_2NHC(NH_2)=$, $R^1$=H, $R^2$=H, $R^3$=absent;
(F) L=$-(CH_2)_2NHC(O)CH_2NHC(NH_2)=$, $R^1$=H, $R^2$=H, $R^3$=absent;
(G) L=$-(CH_2)_3NHC(NH_2)=$, $R^1$=H, $R^2$=H, $R^3$=absent;
(H) L=$-(CH_2)_3-$, $R^1$=H, $R^2$=Me, $R^3$=Me;
(I) L=$-(CH_2)_2-$, $R^1$=H, $R^2$=Me, $R^3$=Me;
(J) L=$-(CH_2)_2NHC(Me)=$, $R^1$=H, $R^2$=H, $R^3$=absent;
(K) L=$-(CH_2)_2NHC(O)CH_2NHC(Me)=$, $R^1$=H, $R^2$=H, $R^3$=absent;
(L) L=$-(CH_2)_3NHC(Me)=$, $R^1$=H, $R^2$=H, $R^3$=absent;
(M) L=$-(CH_2)_2NR^{1'}C(NH_2)=$, $R^1$-$R^{1'}$=$-(CH_2)_2-$, $R^2$=H, $R^3$=absent;
(N) L=$-C(CO_2H)(CH_2)_3-$, $R^1$=H, $R^2$=H, $R^3$=H;
(O) L=$-C(CO_2H)(CH_2)_3NHC(NH_2)=$, $R^1$=H, $R^2$=H, $R^3$=absent;
(P) L=$-C(CO_2H)CH_2-$, $R^1$=H, $R^2$=H, $R^3$=H;
(Q) L=$-C(CO_2H)(CH_2)_2-$, $R^1$=H, $R^2$=H, $R^3$=H;
(R) L=$-C(CO_2H)(CH_2)_4-$, $R^1$=H, $R^2$=H, $R^3$=H;
(S) L=$-C(CO_2H)(CH_2)_3-$, $R^1$=H, $R^2$=Me, $R^3$=Me
(T) L=$-(CH_2)_4-$, $R^1$=H, $R^2$=H, $R^3$=H;
(U) L=$-(CH_2)_5-$, $R^1$=H, $R^2$=H, $R^3$=H;
(V) L=$-(CH_2)_4-$, $R^1$=H, $R^2$=Me, $R^3$=Me;
(W) L=$-CHR^{2'}C(O)-$, $R^1$=H, $R^2$-$R^{2'}$=$-(CH_2)_3-$, $R^3$=H;
(X) L=$CHR^{2'}CH_2$, $R^1$=H, $R^2$-$R^{2'}$=$-(CH_2)_3-$, $R^3$=H;
(Y) L=$-CHR^5CH_2NR^{5'}C(Me)=$, $R^1$=H, $R^2$=H, $R^5$-$R^{5'}$=$-(CH_2)_3-$, $R^3$=absent;

(Z) L=—CHR²'(CH₂)₂—, R¹=H, R²-R²'=—(CH₂)₂—, R³=H;
(AA) L=—(CH₂)₂CHR¹'—, R¹-R¹'=—(CH₂)₂—, R²=H, R³=H;
(AB) L=—(CH₂)₂CHR¹'NHC(O)C(Me)—, R¹-R¹'=—(CH₂)₂—, R²=H, R³=H;
(AC) L=—CH₂CHR¹'—, R¹1-R¹'=—(CH₂)₃—, R²=H, R³=H;
(AD) L=—CH₂CHR¹'NHC(Me)=, R¹-R¹'=—(CH₂)₃—, R²=H, R³=absent;
(AE) L=—CHR⁵(CH₂)₂CHR⁵'—, R¹=H, R²=H, R⁵-R⁵'=—(CH₂)₂—, R³=H.
(AF) L=CHR²'CH₂, R¹=H, R²-R²'=—(CH₂)₃—, R³=Me;
(AG) L=CHR²'CH₂, R¹=H, R²-R²'=—(CH₂)₂—, R³=H;
(AH) L=—CHR²'(CH₂)₂—, R¹=H, R²-R²'=—(CH₂)₂—, R³=Me;
(AI) L=—CHR²'CHR³'(CH₂)₂—, R¹=H, R²-R²'=—CH₂—, R³-R³'=—(CH₂)₂—, R₄=H, X=Cl; or
(AJ) L=—CR⁵=CH—CH=CR⁵'—CH₂—, R⁵-R⁵' is —CH=CH—, R¹=H, R²=H, R³=H, R⁴=H, X=Cl.

15. A method of treating, preventing or suppressing symptoms associated with at least one of:
a) a mood disorder, wherein the mood disorder comprises depression, or wherein the symptoms of the mood disorder include at least one of apathy, persistent feelings of sadness, feelings of hopelessness or helplessness, having low self-esteem, feeling inadequate, excessive guilt, feelings of wanting to die, loss of interest in usual activities or activities once enjoyed, difficulty with relationships, sleep disturbances, changes in appetite or weight, decreased energy, difficulty concentrating, a decrease in the ability to make decisions, suicidal thoughts or attempts, frequent physical complaints, running away or threats of running away from home, hypersensitivity to failure or rejection, irritability, hostility, or aggression; and,
b) headache and/or migraine, wherein the headache comprises tension-type headaches or wherein the migraine comprises common migraine, classic migraine, familial hemiplegic migraine, sporadic hemiplegic migraine, migraine with brainstem aura, retinal migraine, recurrent migraine and chronic migraine, or wherein the treatment eliminates, reduces the severity of, and/or reduces the frequency of occurrence of at least one symptom of tension-type headaches or migraine, which symptom includes at least one of moderate to severe headaches, and associated symptoms including aura, blurred vision, nausea, vomiting, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, cold and moist feeling in appendages, and sensitivity to light, sound, or smell;
the method comprising administering to a subject in need thereof an effective amount of a compound represented by general structure (I):

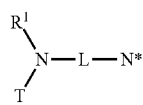

(I)

wherein,
T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;
L is a linker between the amide nitrogen atom and the distal nitrogen atom comprising 1 to 10 optionally substituted backbone atoms selected from carbon, nitrogen and oxygen;
N* is represented by structure (IIa) or (IIb)

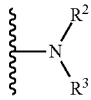

(IIa)

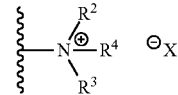

(IIb)

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;
$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with a backbone atom of the linker L in a cyclic structure; and
$R^4$ is selected from hydrogen (H) or $C_1$-$C_6$ alkyl, wherein the alkyl moiety may be substituted with one or more halogen atoms or (halo)alkoxy moieties; and
X is an anion,
wherein the treatment further comprises the administration of an additional active agent selected from the group consisting of a norepinephrine reuptake inhibitor, a selective serotonin reuptake inhibitor, a tricyclic antidepressant, a monoamine oxidase inhibitor, and combinations thereof.

16. A method of treating, preventing or suppressing symptoms associated with at least one of:
a) a mood disorder, wherein the mood disorder comprises depression, or wherein the symptoms of the mood disorder include at least one of apathy, persistent feelings of sadness, feelings of hopelessness or helplessness, having low self-esteem, feeling inadequate, excessive guilt, feelings of wanting to die, loss of interest in usual activities or activities once enjoyed, difficulty with relationships, sleep disturbances, changes in appetite or weight, decreased energy, difficulty concentrating, a decrease in the ability to make decisions, suicidal thoughts or attempts, frequent physical complaints, running away or threats of running away from home, hypersensitivity to failure or rejection, irritability, hostility, or aggression; and, b) headache and/or migraine, wherein the headache comprises tension-type headaches or wherein the migraine comprises common migraine, classic migraine, familial hemiplegic migraine, sporadic hemiplegic migraine, migraine with brainstem aura, retinal migraine, recurrent migraine and chronic migraine, or wherein the treatment eliminates, reduces the severity of, and/or reduces the frequency of occurrence of at least one symptom of tension-type headaches or migraine, which symptom includes at least one of moderate to severe headaches, and associated symptoms including aura, blurred vision, nausea, vomiting, delirium, nasal stuffiness, diarrhea, tinnitus, polyuria, pallor, sweating, localized edema of the scalp or face, scalp tenderness, prominence of a vein or artery in the temple, stiffness and tenderness of the neck, impairment of concentration and mood, cold and moist feeling in appendages, and sensitivity to light, sound, or smell;

the method comprising administering to a subject in need thereof an effective amount of a compound represented by general structure (I):

 (I)

wherein,

T is a water-soluble vitamin E derivative having a core chromanyl or chromanyl quinone framework and a carboxylic acid moiety substituted at the 2-position, wherein T is connected to nitrogen via the carboxylic acid moiety, as such forming an amide moiety;

L is a linker between the amide nitrogen atom and the distal nitrogen atom comprising 1 to 10 optionally substituted backbone atoms selected from carbon, nitrogen and oxygen;

N* is represented by structure (IIa) or (IIb)

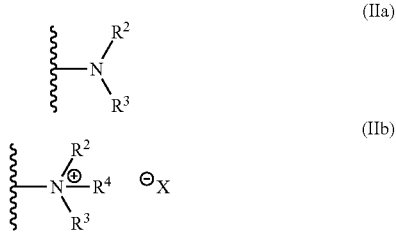

$R^1$ and $R^2$ are each independently selected from hydrogen (H), $C_1$-$C_6$ alkyl or $C_1$-$C_6$ alkenyl, or $R^1$ and $R^2$ are joined together and thus form a second linker between the amide nitrogen atom and the distal nitrogen atom, or $R^1$ is joined with a backbone atom of the linker L in a cyclic structure and/or $R^2$ is joined with a backbone atom of the linker L in a cyclic structure;

$R^3$ is selected from hydrogen (H), $C_1$-$C_6$ alkyl or $C_1$-$C_6$ alkenyl, wherein the alkyl or alkenyl moiety may be substituted with one or more halogen atoms, hydroxyl moieties or (halo)alkoxy moieties, or $R^3$ is absent when the distal nitrogen atom is part of an imine moiety; or optionally $R^3$ is joined with a backbone atom of the linker L in a cyclic structure; and $R^4$ is selected from hydrogen (H) or $C_1$-$C_6$ alkyl, wherein the alkyl moiety may be substituted with one or more halogen atoms or (halo)alkoxy moieties; and X is an anion, wherein the subject to be treated is a primate.

* * * * *